(12) United States Patent
Esterberg et al.

(10) Patent No.: US 11,229,496 B2
(45) Date of Patent: Jan. 25, 2022

(54) SYSTEMS AND METHODS OF PROVIDING ASSISTANCE TO A SURGEON FOR MINIMIZING ERRORS DURING A SURGICAL PROCEDURE

(71) Applicant: NAVLAB HOLDINGS II, LLC, Seattle, WA (US)

(72) Inventors: Justin Esterberg, Mercer Island, WA (US); Jeffrey Roh, Seattle, WA (US)

(73) Assignee: NAVLAB HOLDINGS II, LLC, Seattle, WA (US)

( * ) Notice: Subject to any disclaimer, the term of this patent is extended or adjusted under 35 U.S.C. 154(b) by 465 days.

(21) Appl. No.: 16/015,486

(22) Filed: Jun. 22, 2018

(65) Prior Publication Data

US 2018/0368930 A1   Dec. 27, 2018
US 2019/0239973 A9   Aug. 8, 2019

Related U.S. Application Data

(60) Provisional application No. 62/528,304, filed on Jul. 3, 2017, provisional application No. 62/524,506, filed
(Continued)

(51) Int. Cl.
*A61B 34/00* (2016.01)
*A61B 34/20* (2016.01)
(Continued)

(52) U.S. Cl.
CPC ............ *A61B 34/76* (2016.02); *A61B 34/10* (2016.02); *A61B 34/20* (2016.02); *A61B 34/25* (2016.02); *A61B 34/35* (2016.02); *A61B 34/37* (2016.02); *A61B 90/37* (2016.02); *G06F 3/016* (2013.01); *G06T 17/00* (2013.01); *G06T 19/003* (2013.01); *G06T 19/006* (2013.01); *G06T 19/20* (2013.01); *G16H 20/40* (2018.01); *G16H 30/40* (2018.01);
(Continued)

(58) Field of Classification Search
CPC ................................ A61B 34/20; A61B 34/76
See application file for complete search history.

(56) References Cited

U.S. PATENT DOCUMENTS

2002/0120188 A1*  8/2002  Brock ................. A61B 5/0086
                                                    600/407
2004/0024311 A1*  2/2004  Quaid, III ............. A61B 34/10
                                                    600/428
(Continued)

*Primary Examiner* — Nicholas W Woodall
(74) *Attorney, Agent, or Firm* — Hamre, Schumann, Mueller & Larson, P.C.

(57) ABSTRACT

Systems and methods for providing assistance to a surgeon for minimizing errors during a surgical procedure are disclosed. A method includes creating a Three-Dimensional (3D) model of a patient using at least one image of an affected area of the patient. Surgical paths are retrieved for performing a surgical procedure. A surgical path, selected by a surgeon, may be displayed as overlaid on the 3D model. A haptic barrier and a hard barrier may be defined for different types of tissues and feedbacks may be associated with the haptic barrier and the hard barrier. Position of a surgical tool of a robotic surgical system may be monitored in real-time during a surgical procedure. Movement of the surgical tool into one of the haptic barrier and the hard barrier may be detected and a suitable feedback may be provided, based on the movement.

10 Claims, 19 Drawing Sheets

Related U.S. Application Data on Jun. 24, 2017, provisional application No. 62/523,777, filed on Jun. 23, 2017, provisional application No. 62/523,264, filed on Jun. 22, 2017.

(51) Int. Cl.

| | | |
|---|---|---|
| *A61B 34/30* | (2016.01) | |
| *A61B 34/10* | (2016.01) | |
| *G06T 19/00* | (2011.01) | |
| *G06T 17/00* | (2006.01) | |
| *G06T 19/20* | (2011.01) | |
| *A61B 34/35* | (2016.01) | |
| *A61B 90/00* | (2016.01) | |
| *G06F 3/01* | (2006.01) | |
| *G16H 50/30* | (2018.01) | |
| *G16H 40/63* | (2018.01) | |
| *G16H 50/50* | (2018.01) | |
| *A61B 34/37* | (2016.01) | |
| *G16H 20/40* | (2018.01) | |
| *G16H 30/40* | (2018.01) | |
| *A61B 17/16* | (2006.01) | |
| *A61B 17/3211* | (2006.01) | |
| *A61B 17/00* | (2006.01) | |
| *A61B 90/50* | (2016.01) | |

(52) U.S. Cl.
CPC .......... G16H 40/63 (2018.01); G16H 50/30 (2018.01); G16H 50/50 (2018.01); *A61B 17/1626* (2013.01); *A61B 17/3211* (2013.01); *A61B 90/03* (2016.02); *A61B 2017/00119* (2013.01); *A61B 2017/00203* (2013.01); *A61B 2034/105* (2016.02); *A61B 2034/107* (2016.02); *A61B 2034/2057* (2016.02); *A61B 2034/2065* (2016.02); *A61B 2034/254* (2016.02); *A61B 2034/256* (2016.02); *A61B 2034/744* (2016.02); *A61B 2090/364* (2016.02); *A61B 2090/365* (2016.02); *A61B 2090/372* (2016.02); *A61B 2090/378* (2016.02); *A61B 2090/502* (2016.02); *G06T 2200/08* (2013.01); *G06T 2210/41* (2013.01); *G06T 2219/004* (2013.01); *G06T 2219/2012* (2013.01)

(56) References Cited

U.S. PATENT DOCUMENTS

| | | | |
|---|---|---|---|
| 2004/0106916 A1* | 6/2004 | Quaid | A61B 34/76 606/1 |
| 2004/0128026 A1* | 7/2004 | Harris | A61B 34/76 700/245 |
| 2005/0154295 A1* | 7/2005 | Quistgaard | A61B 8/00 600/424 |
| 2006/0100505 A1* | 5/2006 | Viswanathan | A61B 34/20 600/424 |
| 2006/0142657 A1* | 6/2006 | Quaid | A61B 17/1764 600/424 |
| 2007/0270685 A1* | 11/2007 | Kang | A61B 17/1764 600/424 |
| 2009/0228145 A1* | 9/2009 | Hodgson | A61B 17/1757 700/258 |
| 2015/0057493 A1* | 2/2015 | Harris, Jr. | A63F 13/24 600/38 |
| 2019/0069957 A1* | 3/2019 | Barral | A61B 34/30 |
| 2020/0015902 A1* | 1/2020 | Scheib | A61B 5/6886 |

* cited by examiner

SYSTEMS AND METHODS OF PROVIDING ASSISTANCE TO A SURGEON FOR MINIMIZING ERRORS DURING A SURGICAL PROCEDURE

CROSS-REFERENCE TO RELATED APPLICATION

This Application claims priority from U.S. Provisional Application Nos. 62/523,264, filed Jun. 22, 2017; 62/523,777, filed Jun. 23, 2017; 62/528,304, filed Jul. 3, 2017; and 62/524,506, filed Jun. 24, 2017.

FIELD OF THE DISCLOSURE

The present disclosure is generally related to providing surgical assistance, and more particularly related to providing the surgical assistance in robotic surgical systems.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Each surgical procedure has a different level of associated risk. The risk may arise due to a patient's health before surgery and any errors that might occur during surgery. To minimize the risks arising due to a patient's health, a pre-operative evaluation is generally performed. The pre-operative evaluation is performed to learn about the patient's medical history. The pre-operative evaluation may include, e.g., physical examination, neurological examination, etc. The pre-operative evaluation enables a medical staff to take proactive steps for reducing the risks associated with the surgical procedure.

Based on the pre-operative evaluation, a surgeon may determine which surgical procedure is to be performed on the patient. The surgeon may also practice the surgical procedures beforehand. The surgeon may practice using Virtual Reality (VR) systems.

During the practice, the surgeon may refer to data presented via VR glasses or is projected on an external display. The external display may show images of the patient, using cameras integrated in an operation theatre or surgical equipment operated by the surgeon. Use of an external display may distract the surgeon. Sometimes, touch-screens are used as interactive displays for receiving input and providing feedback related to the surgical procedure, but operating a touch screen is not a practical task for a surgeon during surgery.

In VR simulation training, surgeons require robust surgical tools for performing surgical procedures, e.g., a robotic surgical arm. Such tools are used to improve a surgeon's competencies for performing specific tasks by providing greater control during each stage of a surgical procedure. Also, VR simulation training improves efficiencies in terms of time and cost for surgical procedures. However, true integration of imaging (pre-operative and intra-operative) and surgical access has not been accomplished. Thus, the burden lies on a surgeon to cognitively integrate all available information.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the FIGS. represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the FIGS. are not necessarily to scale, emphasis instead being placed upon illustrating principles.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several FIGS., and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1A:
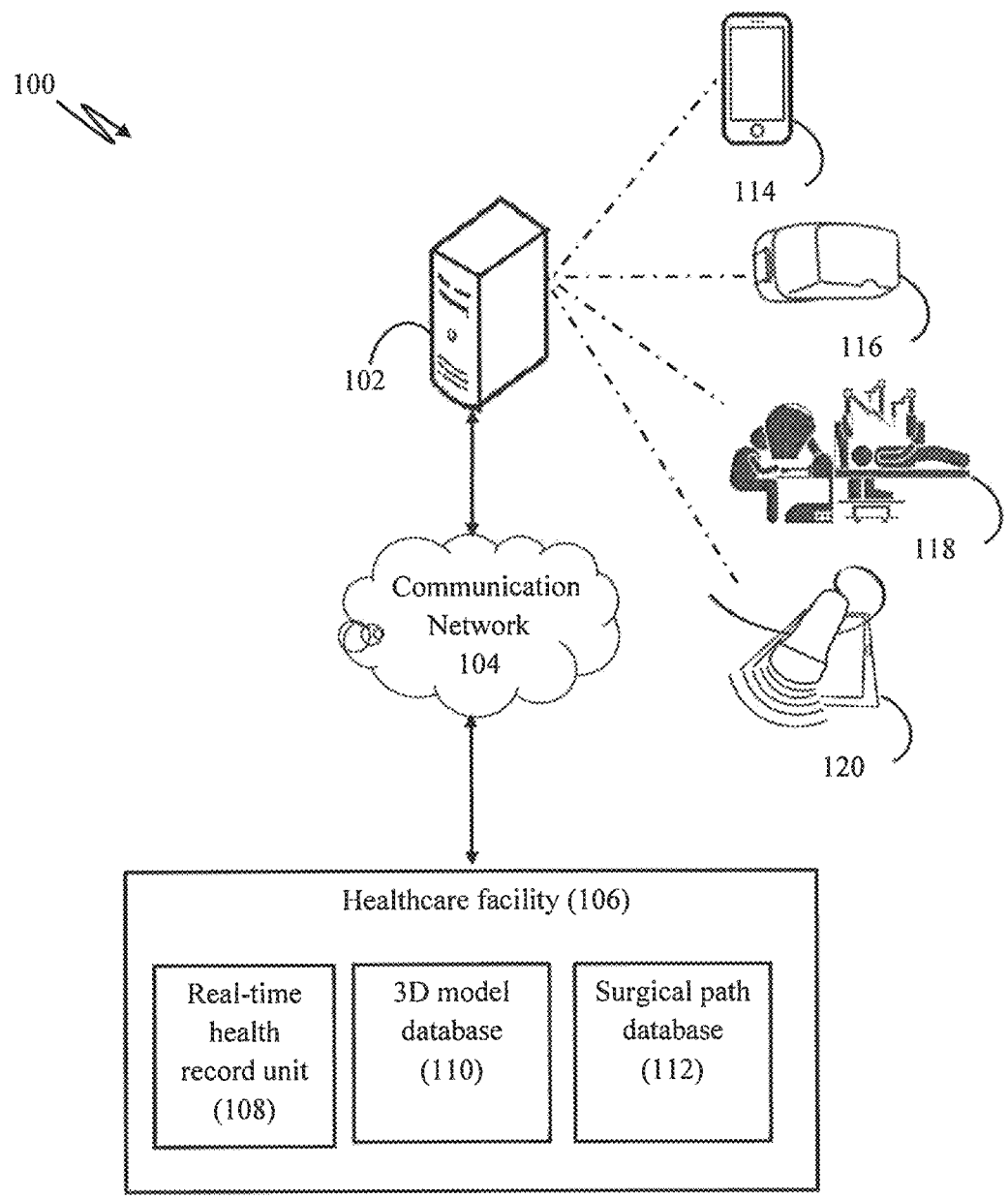
FIG. 1A illustrates a network connection diagram 100 of a system 102 for providing assistance to a surgeon for minimizing errors during a surgical procedure, according to an embodiment.

FIG. 1A illustrates a network connection diagram 100 of a system 102 for providing assistance to a surgeon for minimizing errors during a surgical procedure, according to an embodiment. The system 102 may be connected with a communication network 104. The communication network 104 may further be connected to a healthcare facility 106 to facilitate data transfer between the system 102 and the healthcare facility 106.

The communication network 104 may be a wired and/or a wireless network. The communication network 104, if wireless, may be implemented using communication techniques such as Visible Light Communication (VLC), Worldwide Interoperability for Microwave Access (WiMAX), Long Term Evolution (LTE™), Wireless Local Area Network (WLAN), Infrared (IR) communication, Public Switched Telephone Network (PSTN), Radio waves, and other communication techniques known in the art.

The healthcare facility 106 may include a real-time health record unit 108 for storing data related to patients. The healthcare facility may further comprise a Three-dimensional (3D) model database 110 and a surgical path database 112. In at least one embodiment, data stored in the 3D model database 110 and the surgical path database 112 may also be stored in a memory 206 of the system 102 (see FIG. 2A). Different databases are presently illustrated and described; however, a single database may also be used for storing the data. Usage of the different databases may also allow segregated storage of different data, and may thus reduce time to access required data.

In at least one embodiment, the 3D model database 110 may store 3D models of affected areas of patients. The 3D models may be created using images captured using different sources and may include, but not be limited to, camera images, Magnetic Resonance Imaging (MRI) images, ultrasound images, and X-Ray images. The 3D models may include all of the areas or types of tissues, classified by the surgeon as either of a haptic barrier and a hard barrier.

In at least one embodiment, the surgical path database 112 may store details regarding methods of performing various surgical procedures by a robotic surgical system 118. The surgical path database 112 may also store different methods and paths for performing respective surgical procedures.

Figure 1B:
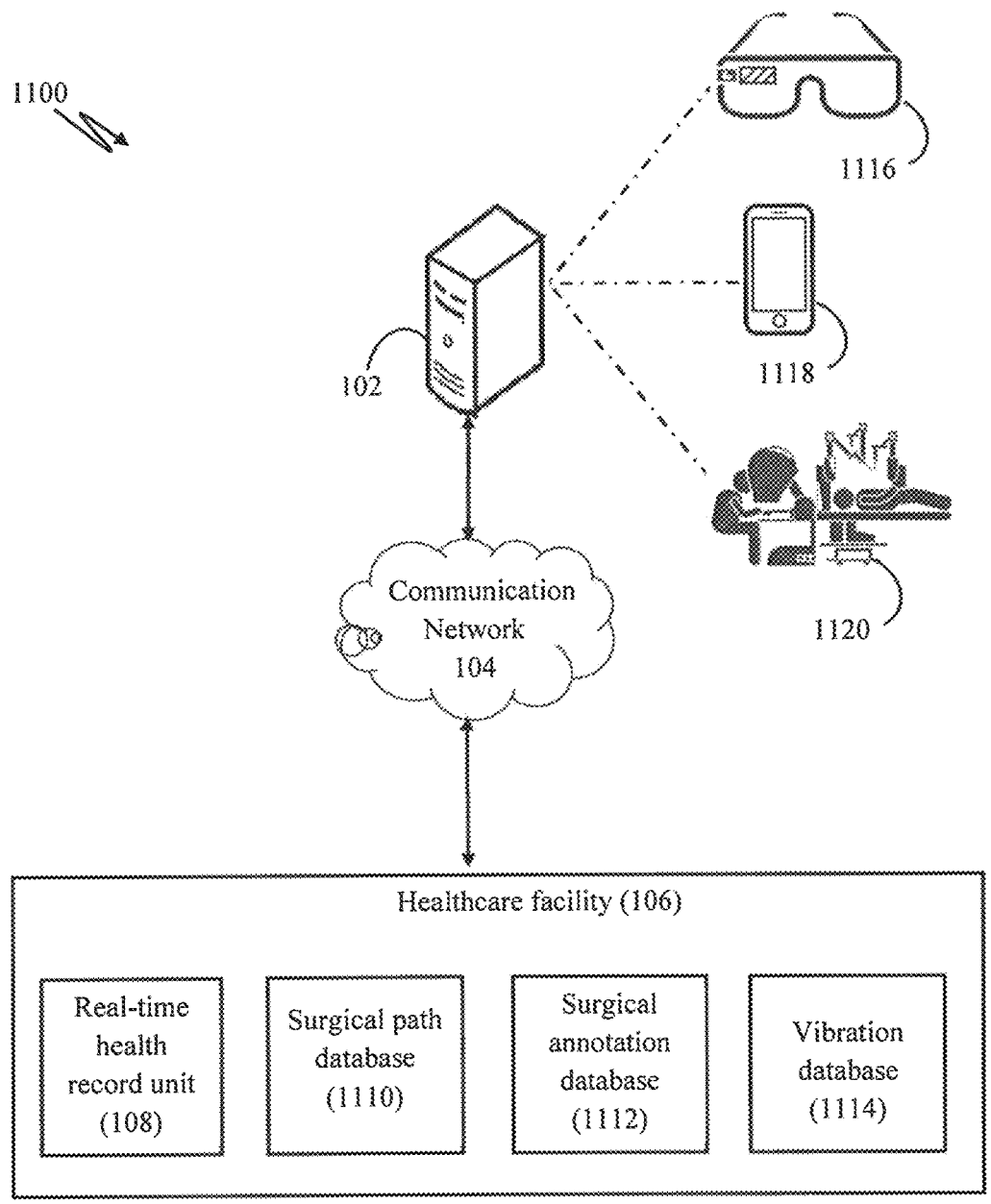
FIG. 1B illustrates another network connection diagram 1100 of system 102 for assisting a surgeon with visual feedback and haptic feedback during a surgical procedure, according to an embodiment.

FIG. 1B illustrates a network diagram 100 of the system 102, which may also be utilized to assist a surgeon by providing at least one of visual feedback or haptic feedback during a surgical procedure, according to an embodiment. The system 102 may be connected to a communication network 104. As with the depiction and description of FIG. 1A, the communication network 104 may further be connected with a healthcare facility 106 to facilitate data transfer between the system 102 and the healthcare facility 106.

The communication network 104 may be a wired and/or a wireless network, as depicted and described with regard to FIG. 1A.

The healthcare facility 106, further to the description pertaining to the depiction in FIG. 1A, may also include the real-time health record unit 108 and more databases for storing different information that may be utilized during a surgical procedure. The group of databases may include a surgical path database 1110, surgical annotation database 1112, and a vibration database 1114. Different databases are presently illustrated and described; however, a single database may also be used for storing the data. Usage of the different databases may also allow segregated storage of different data, and may thus reduce time to access required data.

The real-time health record unit 108 may be further configured to store data of patients in a real-time. The data may correspond to medical imaging data and/or diagnostic data, e.g., medical records of the patients, such as medical history of the respective patients test results, and notes of surgeons/doctors or other health-care providers.

In at least one embodiment, the surgical path database 1110 may store surgical paths that may be followed for a particular type of surgical procedure. It should be noted that different paths, i.e., surgical paths, may be used for performing any surgical procedure. Data pertaining to all surgical paths may be stored in the surgical path database 1110, the data including details and instructions for each surgical path, assignments for surgical attendees, required tools and resources for the surgical paths, viable responses for adverse conditions for the respective surgical paths, etc.

In at least one embodiment, the surgical annotation database 1112 may be configured to accept annotations provided by the surgeon, either during surgical practice or training session as well as during the preplanning stage, or even during an actual surgical procedure. A surgeon may add annotations at any time during a virtual reality simulation, and the annotations may be stored in the surgical annotation database 1112. The surgeon may add the annotations either using the system 102 or a user device 1118. A smart phone is shown as the user device 1118 in FIG. 1B, as a non-limiting example, although any user device 1118 capable of displaying a GUI, e.g., a laptop, a desktop, a tablet, a phablet, etc., may be utilized as user device 1118.

In at least one embodiment, the vibration database 1114 may be configured to store information related to deviation margins, ranges, or windows along a surgical path that may be selected by a surgeon. Information related to the deviation margins may be used to provide haptic feedback to the surgeon, via, e.g., a haptic feedback hand controller.

Figure 1C:
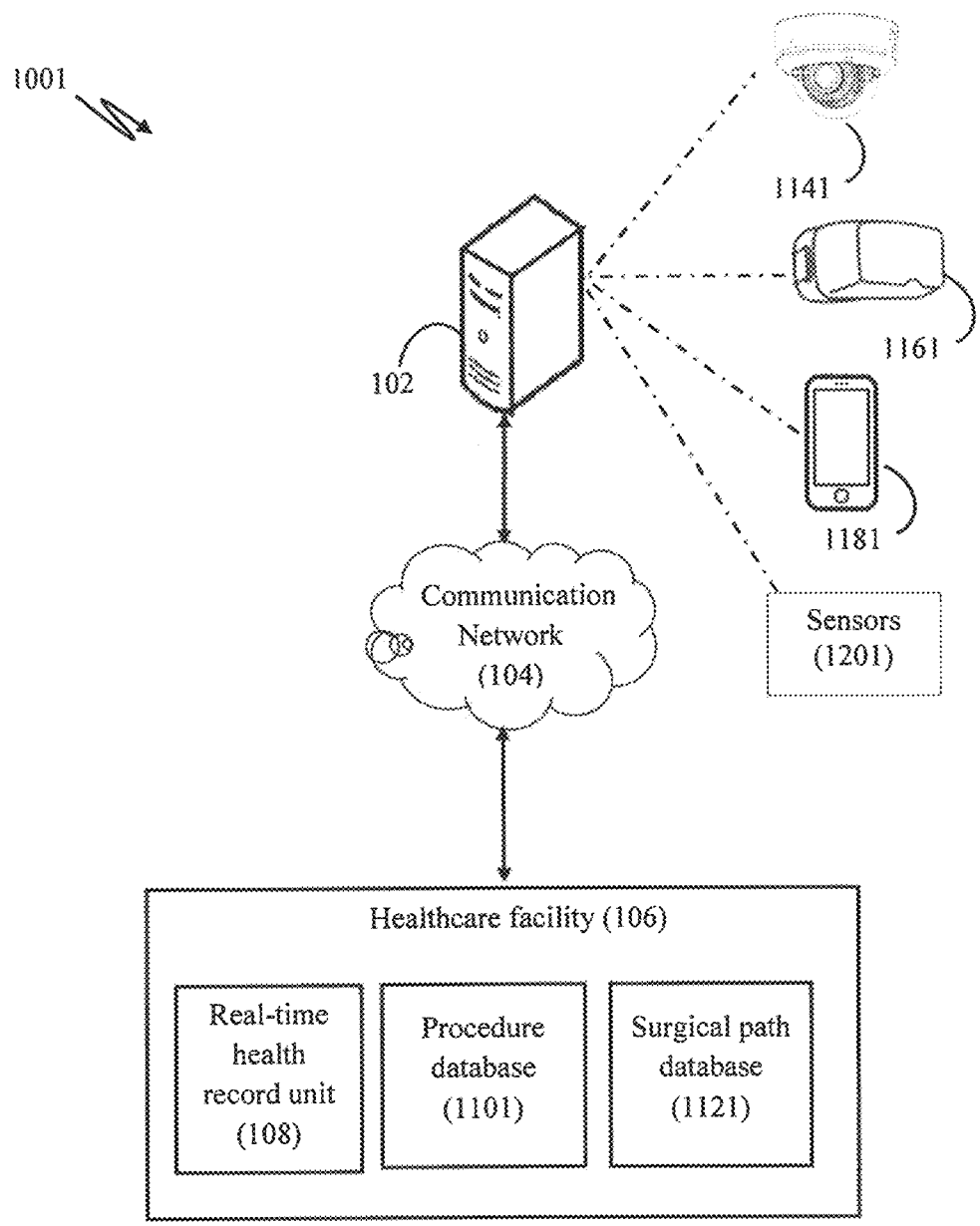
FIG. 1C illustrates another network connection diagram 1001 of system 102 for guiding a surgeon in real-time during a medical procedure, according to an embodiment.

FIG. 1C illustrates a network diagram 100 of a system 102, which may also be utilized to provide real-time guidance to a surgeon during a medical procedure, according to an embodiment. The system 102 may be connected to a communication network 104. As with the depiction and description of FIG. 1A, the communication network 104 may further be connected with a healthcare facility 106 to facilitate data transfer between the system 102 and the healthcare facility 106.

The communication network 104 may be a wired and/or a wireless network, as depicted and described with regard to FIG. 1A.

The healthcare facility 106, further to the description pertaining to the depictions in FIGS. 1A and 1B, may also include a real-time health record unit 108 for storing data related to patients and more databases for storing different information that may be utilized during a medical procedure. The group of databases may further include a procedure database 1101 and a surgical path database 1121. In at least one embodiment, data stored in the procedure database 1101 and the surgical path database 1121 may also be stored in a memory 206 of the system 102 (see FIG. 2C). Different databases are used in present case; however, a single database may also be used for storing the data. Usage of the different databases may also allow segregated storage of different data and may thus reduce time to access required data.

In at least one embodiment, the procedure database 1101 may store videos and sensor data pertaining to previously performed surgical procedures. The videos and sensor data are recorded in real-time during a surgical procedure and stored in the procedure database 1101. The stored video and surgical data may be used by a surgeon in selecting a surgical procedure for a patient and, more specifically, a particular surgical path based on a medical need of the patient.

In at least one embodiment, the surgical path database 1121 may store data pertaining to methods for performing various surgical procedures. The surgical path database 1121 may also store information and data pertaining to different methods and paths for performing each surgical procedure. The surgeon may access the surgical path database 1121 using a user device 1181, connected to the system 102. A smart phone is shown as the user device 1181 in FIG. 1C, as a non-limiting example, although any user device 1181 capable of displaying a GUI, e.g., a laptop, a desktop, a tablet, a phablet, e.g, may be utilized as user device 1181.

Figure 2A:
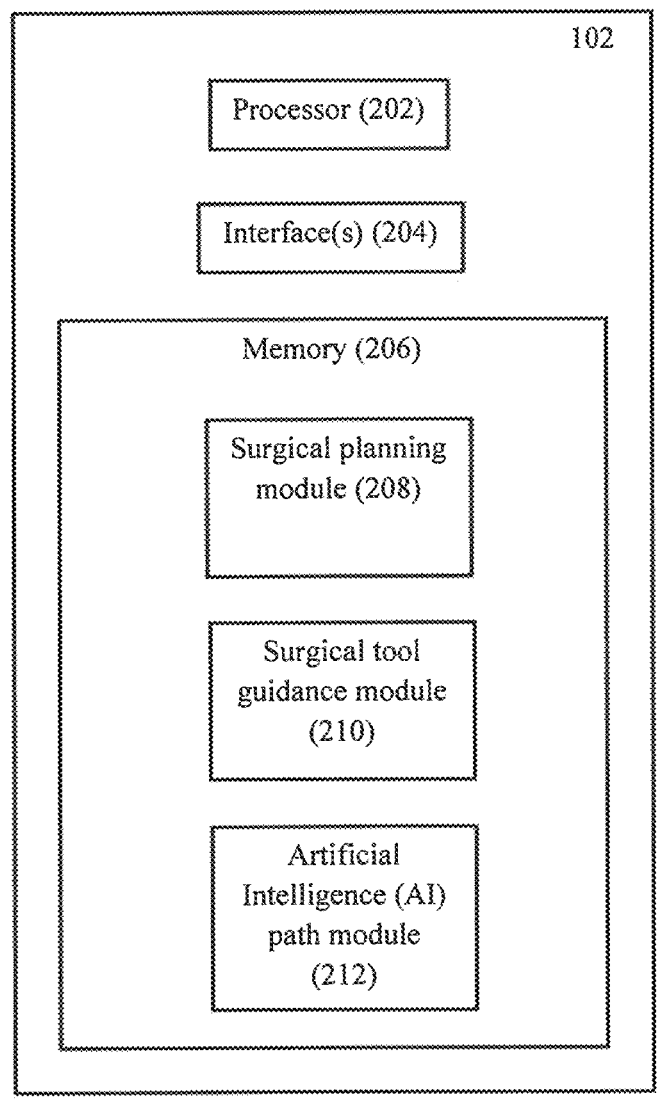
FIG. 2A illustrates a block diagram showing different components of system 102, according to an embodiment.

FIG. 2A depicts a block diagram showing different components of the system 102, as in the non-limiting illustration of FIG. 1A. The system 102 includes a processor 202, interface(s) 204, and the memory 206. The processor 202 may execute an algorithm stored in the memory 206 to provide assistance to a surgeon during a surgical procedure. The processor 202 may also be configured to decode and execute any instructions received from one or more other electronic devices or server(s).

In at least one embodiment, the processor 202 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 202 may be configured to execute one or more computer-readable program instructions, such as program instructions to carry out any of the functions described in this description.

The interface(s) 204 may facilitate interaction between a surgeon and the system 102. The interface(s) 204 of the system 102 may either accept an input from the user or provide an output to the user, or may perform both the actions. The interface(s) 204 may either be a Command Line Interface (CLI), Graphical User Interface (GUI), or a voice interface.

The memory 206 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read Only Memories (PROMs), Erasable PROMs (EPROMs), Electrically Erasable PROMs (EEPROMs), flash memory, magnetic or optical cards, or other type of media/machine-readable medium suitable for storing electronic instructions.

The memory 206 may comprise modules, implemented as programmed instructions executed by the processor 202. The modules may comprise a surgical planning module 208 and a surgical tool guidance module 210.

Figure 2B:
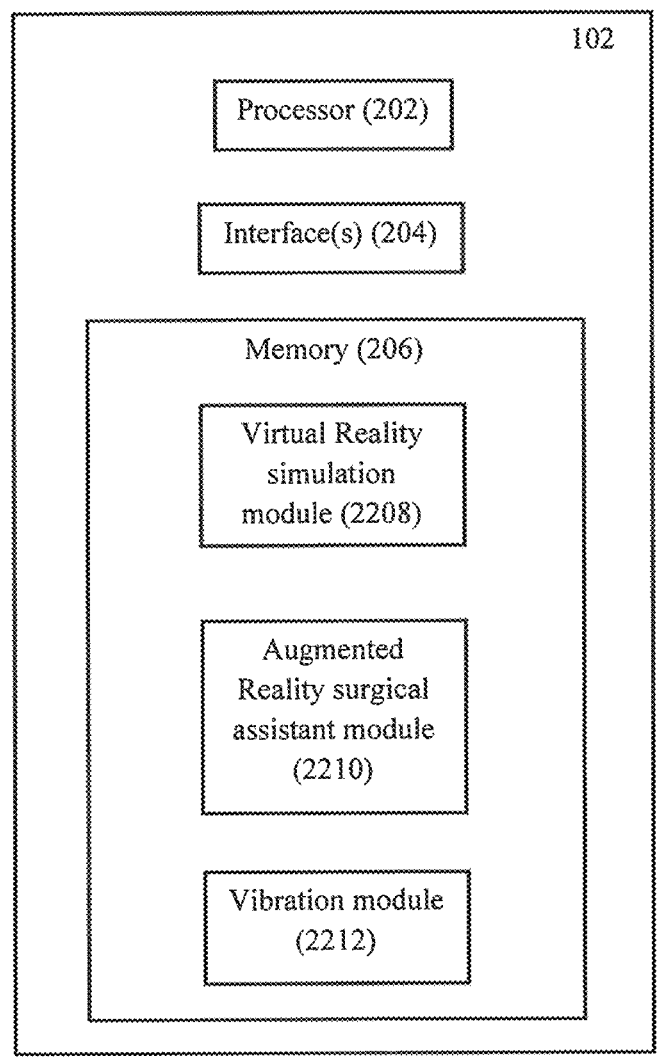
FIG. 2B illustrates a block diagram showing different components of system 102, according to an embodiment.

FIG. 2B depicts a block diagram showing different components of the system 102, as also shown and described with regard to FIG. 2A. The system 102 comprises a processor 202, as also shown and described with regard to FIG. 2A, interface(s) 204, and memory 206, also as shown and described with regard to FIG. 2A. The processor 202 may further execute an algorithm stored in the memory 206 to provide a surgeon with at least one of visual feedback or haptic feedback during a surgical procedure. The processor 202 may also be configured to decode and execute any instructions received from one or more other electronic devices or server(s).

The interface(s) 204, as also shown and described with regard to FIG. 2A, may facilitate interaction between a user and the system 102. The interface(s) 204 of the system 102 may accept input from the user and/or provide output to the user.

In at least one embodiment, the memory 206, as also shown and described with regard to FIG. 2A, may further include three modules, i.e., Virtual Reality (VR) simulation module 208, Augmented Reality (AR) surgical assistant module 210, and vibration module 212.

Figure 2C:
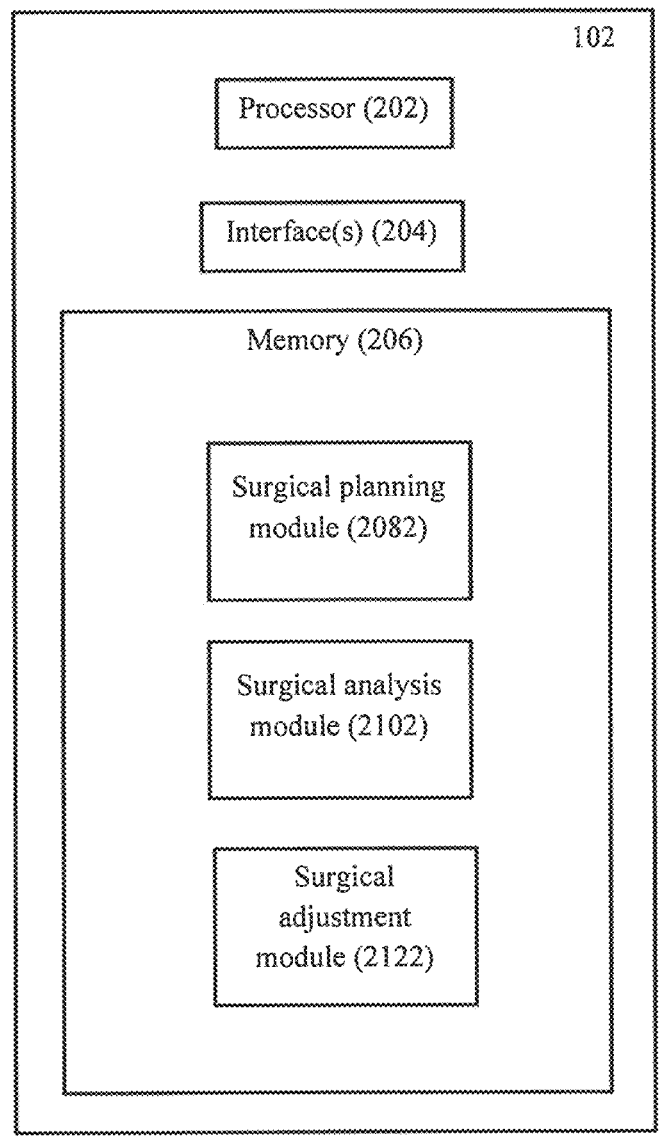
FIG. 2C illustrates a block diagram showing different components of system 102, according to an embodiment.

FIG. 2C shows a block diagram showing different components of the system 102, as also shown and described with regard to FIGS. 2A and 2B. The system 102 includes a processor 202, as also shown and described with regard to FIGS. 2A and 2B, interface(s) 204, and the memory 206, as also shown and described with regard to FIGS. 2A and 2B. The processor 202 may further execute an algorithm stored in the memory 206 providing real-time guidance to a surgeon during the surgical procedure. The processor 202 may also be configured to decode and execute any instructions received from one or more other electronic devices or server(s).

The interface(s) 204 may facilitate interaction between a surgeon and the system 102.

The memory 206 may include modules, implemented as programmed instructions executed by the processor 202. The modules may include a surgical planning module 208, surgical analysis module 210 and a surgical adjustment module 212.

Figure 3A:
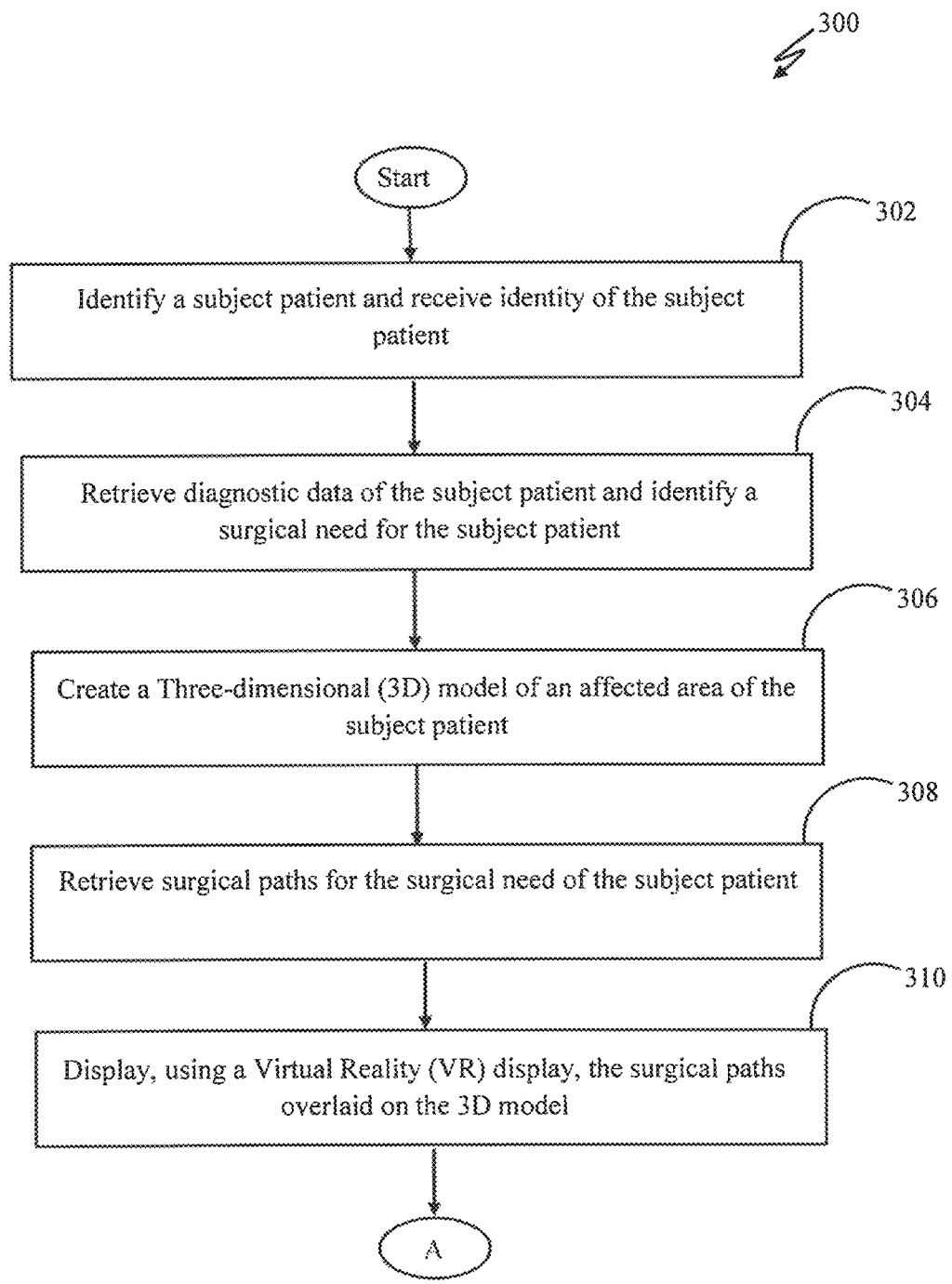
FIGS. 3A and 3B collectively illustrate a flowchart 300 showing a method executed by a surgical planning module 208 of the system 102, according to an embodiment.
Figure 3B:
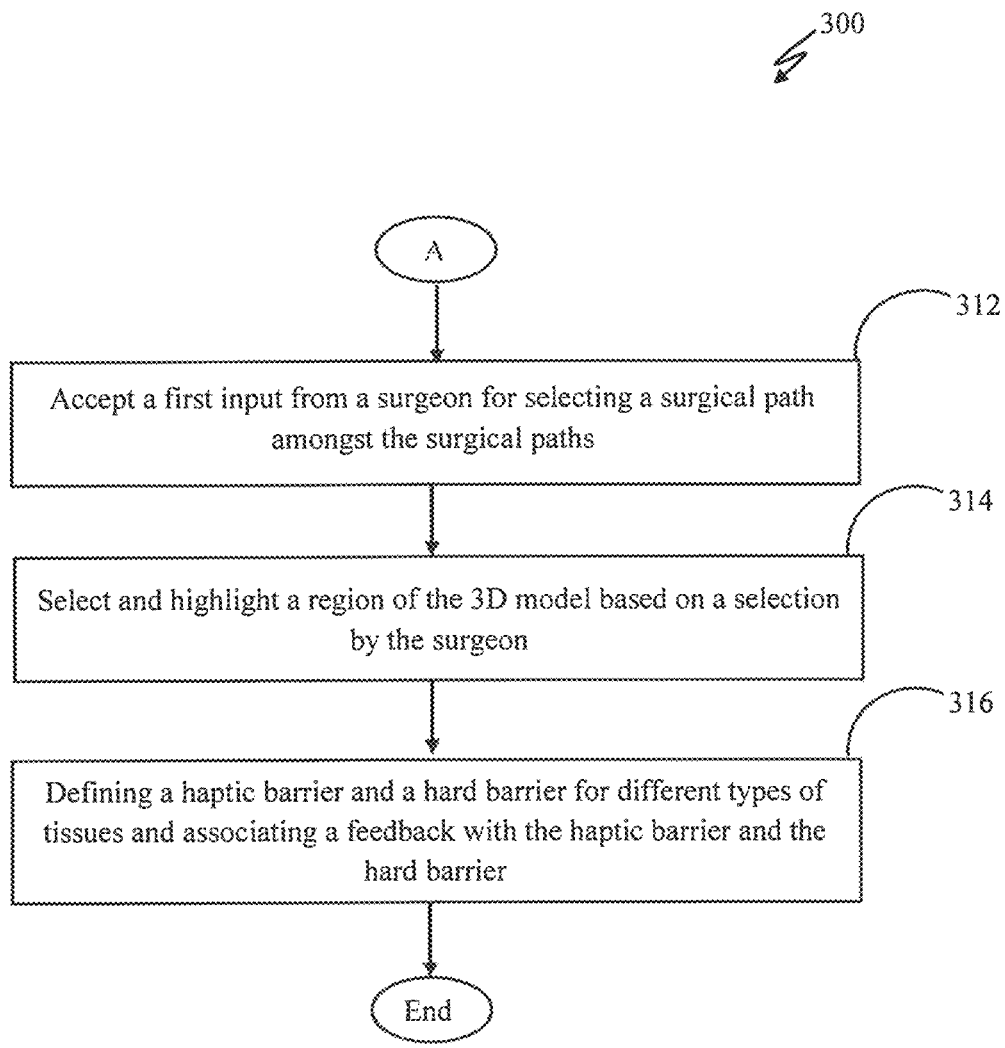

Flowchart 300 in FIGS. 3A and 3B is described hereafter to explain at least one embodiment of the functionality of surgical planning module 208, also shown and described with regard to FIG. 2A. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

A surgeon may log-on to the system 102 using authentication details, such as a user identity, a password, biometric credentials, etc. The log-in process may be implemented by, e.g. accessing the interface 204 of the system 102 or by accessing the user device 114, e.g., smart phone connected to the system 102. Other non-limiting examples of the user device 114 may include, but not be limited to, a laptop, a desktop, a tablet, a phablet, or other such devices known in the art.

At step 302, upon logging-in into the system 102, the surgical planning module 208 may facilitate subject patient identification for the surgeon or other user, and may subsequently receive an identity of the subject patient. The surgical planning module 208 may store and facilitate retrieval of identification details of the subject patient, for whom surgery is intended, from the real-time health record unit 108.

At step 304, the subject patient's diagnosis may be retrieved and a recommended surgery may be identified for the subject patient. The recommended surgery may be identified based on an analysis of the subject patient's diagnosis. Thereafter, at step 306, a Three-Dimensional (3D) model may be prepared of the entire body of the subject patient or just the affected area for which the surgery is recommended. The 3D model may be created using the images captured using different sources, as described above using known image recombination techniques. In at least one embodiment, the 3D model for the subject patient may be stored in the 3D model database 110.

At step 308, possible surgical paths for the recommended surgery for the subject patient may be retrieved. In at least one embodiment, the surgical paths may be stored in and retrieved from the surgical path database 112. Each surgical path may represent potential steps of action taken during a particular iteration of the recommended surgery. The surgical paths may have been previously defined by the surgeon, subject utter experts, or an Artificial Intelligence (AI) path module 212. The AI path module 212 may be configured to analyze images of a particular operative region from multiple patients who have previously undergone the recommended surgery, and also store the outcomes of those surgical procedures for each of the multiple patients. Upon analysis, the AI path module 212 may present the surgeon with data pertaining to any number of the previously implemented surgical paths, unique surgical paths, and frequently used surgical paths along their respective outcomes.

At step 310, the surgical paths may be displayed as being overlaid on the 3D model. In at least one embodiment, the surgical paths, overlaid on the 3D model, may be displayed using a Virtual Reality (VR) display 116. At step 312, the surgeon or other surgery participant may be allowed to select a surgical path from the retrieved surgical paths. Then, the selected surgical path may be displayed as overlaid on the 3D model.

In an exemplary embodiment, the subject patient may require spine disc repair on cervical spine. Images of the subject patient's neck may be used to create a 3D model of the neck. Successively, all surgical paths for performing the surgical procedure on the subject patient's neck may be retrieved from the surgical path database 112. All the surgical paths may be displayed over the 3D model of the subject's neck. Further to the example, the surgeon may select a particular surgical path, from among the retrieved surgical paths, to be overlaid on the 3D model of the subject's neck. The surgeon may select the particular surgical path based upon a comparison and/or review of medical results of other patients having undergone the same or similar surgical procedure using the same particular surgical path.

Overlaying of the particular surgical path on the 3D model of the subject's neck may be performed using a "sizing and matching software tool," which may determine features such as color, shape, and size of the particular surgical path and the 3D model of the subject's neck for providing a precise overlay. If, for example, the "sizing and matching software tool" is not be available for use, the surgeon may be simultaneously presented with a selected surgical path, images of the subject patient, and the 3D model of the affected area of the subject patient. The surgeon may be allowed to either copy and paste or draw the selected surgical path on the 3D model.

At step 314, the surgical planning module 208 may facilitate a selection of a region of the 3D model. In at least one example, the selected region, which may be highlighted, may facilitate identification of a type of tissue in the affected area, thus enabling the surgeon to define the haptic barrier and the hard barrier for the different types of tissues. At step 316, the surgeon may associate a feedback with the haptic barrier and the hard barrier. Further to the example, the haptic barrier and the hard barrier may be defined, by the surgeon, based on a level of cautiousness associated with each type of tissue. For example, skin cells, muscles, and bones may be associated with a lower level of cautiousness and thus, the surgeon may set a haptic barrier and may define haptic feedback for such cells. In another example, blood vessels and cells or brain and Central Nervous System (CNS) may be associated with a highest level of cautiousness. Thus, the surgeon may set a hard barrier and may program to stop progress of the robotic surgical system 118 completely, during intrusion into such cells.

Figure 4:
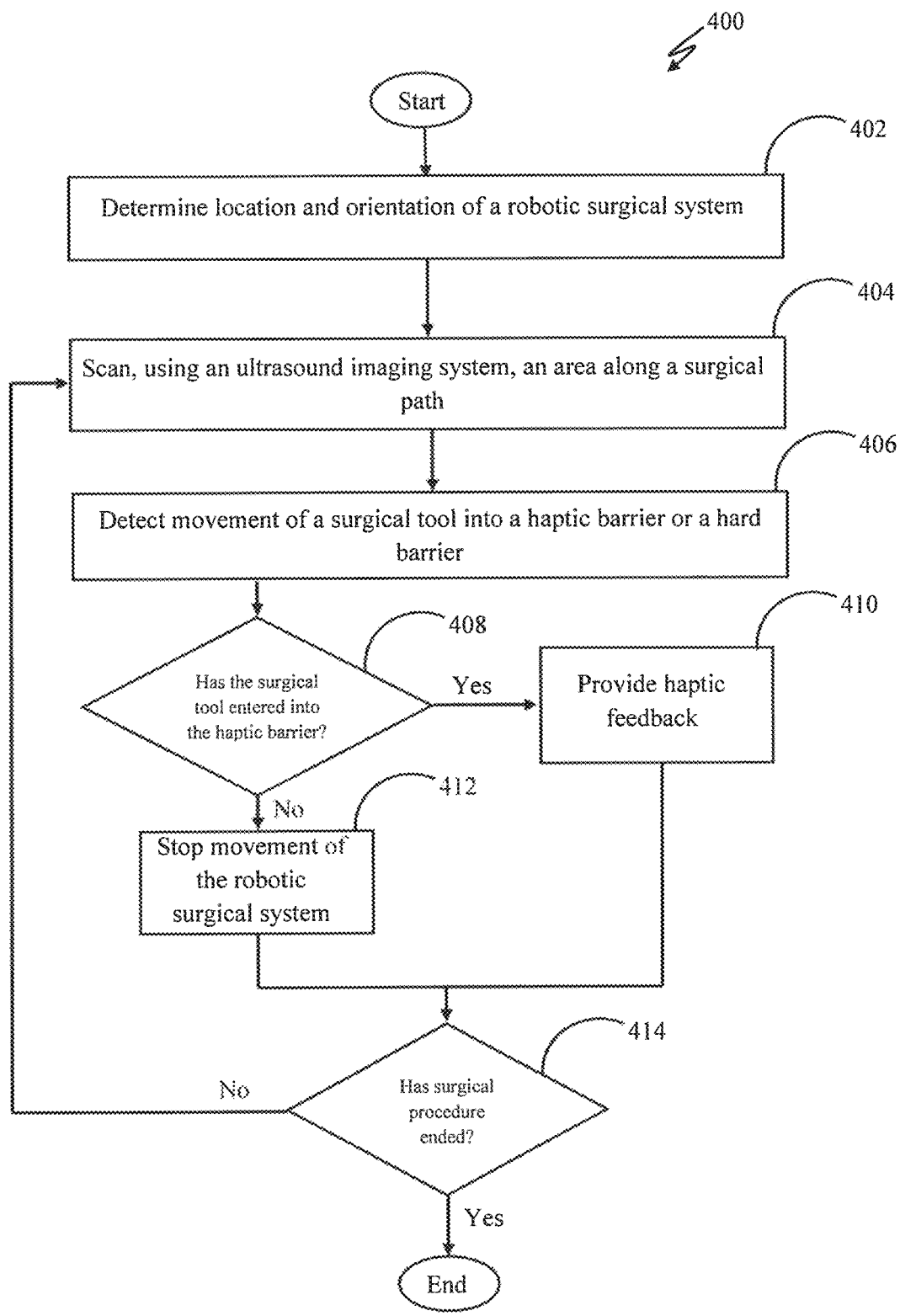
FIG. 4 illustrates a flowchart 400 showing a method executed by a surgical tool guidance module 210 of the system 102, according to an embodiment.

Flowchart 400 in FIG. 4 is described hereafter to explain at least one embodiment of the the functionality of the surgical tool guidance module 210, also shown and described with regard to FIG. 2A. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

A surgeon may log-on to the system 102 using authentication details, such as the user identity, a password, biometric credentials, etc. The log-in process may be implementing by accessing the interface 204 of the system 102 or by accessing the user device 114 connected to the system 102. Subsequently, the surgeon may identify the subject patient to be operated and activate the robotic surgical system 118 to be used for performing the surgical procedure.

At step 402, a location and orientation of the robotic surgical system 118 may be determined using, for example, an ultrasound imaging system 120. The location and orientation may be determined with reference to position of the ultrasound imaging system 120 and position of the subject patient as well.

At step 404, an area determined by the surgical path selected by the surgeon may be scanned. In at least one embodiment, the scanning may be performed using the ultrasound imaging system 120; however, other scanning devices and methods could also be used in different embodiments. At step 406, the area along the surgical path may be scanned to identify movement of a surgical tool of the robotic surgical system 118, into any of the haptic barrier or the hard barrier. The surgical tool may be a drill, scalpel, or any other device used by the surgeon for performing the surgical procedure.

At step 408, while the surgical tool enters into one of the barriers (haptic barrier and hard barrier), the surgical tool guidance module 210 may determine whether or not the surgical tool has entered into the haptic barrier. If the surgical tool has entered into the haptic barrier, at step 410, haptic feedback will be provided to the surgeon. In at least one example, the haptic feedback may be provided to the surgeon by haptic controllers, which may be present on the surgical tool or may be present over gloves worn by the surgeon. Other haptic feedback sensors and devices may also be used in different embodiments, and the surgeon may customize a level and type of haptic feedback based on categories of different types of tissues.

In another example, while the surgical tool is not found to have entered into the haptic barrier, the presence of the surgical tool within or beyond the hard barrier may be determined. Thus, at step 412, the surgical tool guidance module 210 may stop progress or movement of the surgical tool, preventing intrusion of the surgical tool into critical tissue. For example, the surgical tool operated by the surgeon may enter into a critical area such as the Central Nervous System (CNS), and upon detection of such activity, the surgical tool guidance module 210 may immediately stop the robotic surgical system 118 completely to stop any damage. Although the surgical procedure has not ended, returning to step 404, the ultrasound imaging system 120 may again start scanning the area along the surgical path. Further, the robotic surgical system 118 may continue to work after the surgeon removes the surgical tool from the hard barrier.

In at least one example embodiment, the ultrasound imaging system 120 may detect the surgical tool approaching a vital artery, reaching a haptic barrier, preset as, e.g., "3 mm.". The haptic controllers present on the surgical tool may activate and start vibrating, to alert the surgeon. Alternatively, an audible alarm may sound and/or a pre-recorded message may be played. For example, the message may read as "the boundary to the artery is now 4 mm."

In another example embodiment, the ultrasound imaging system 120 may detect the surgical tool approaching a movable muscle, reaching a haptic barrier, preset, e.g., as "2 mm." The haptic controllers present on the surgical tool may activate and start vibrating, to indicate alert the surgeon. Alternatively, an audible alarm may sound and/or a pre-recorded message may be played. For example, the message may read as "within a range of muscle, prepare to move and clamp off muscle out of way".

In yet another example embodiment, the ultrasound imaging system 120 may detect the surgical tool touching a bone on which surgery is to be performed. An audible alarm may sound and/or a pre-recorded message may be played. For example, the message may read as "on the bone, it is now ok to ramp up speed".

In still another example embodiment, the ultrasound imaging system 120 may detect that the surgical tool has drilled up to or past a predetermined threshold length in a bone. An audible alarm may sound and/or a pre-recorded message may be played. For example, the message may read as "pilot hole completed, back off drill."

Figure 5:
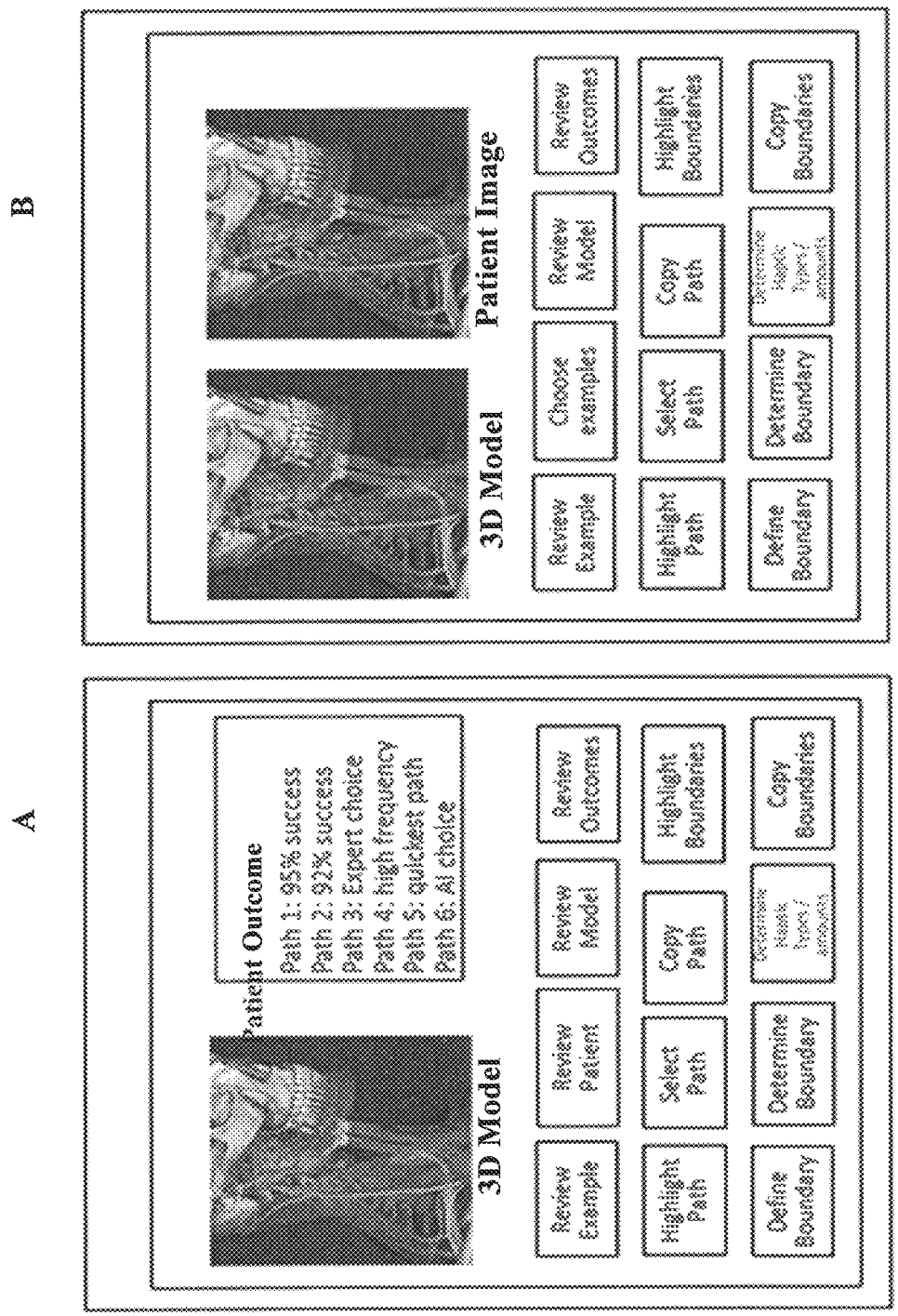
FIG. 5 illustrates a Graphical User interface (GUI) of the system 102, for allowing the surgeon to interact with the surgical planning module 208, according to an embodiment.

FIG. 5 shows a Graphical User Interface (GUI) of the system 102 to facilitate interaction between the surgeon and the surgical planning module 208. Section A of the GUI is a sample representation of the GUI display when the surgeon selects a 3D model from the stored historical data of other patients, including details and information associated with the surgical paths and outcomes of surgery on those other patients. Section B is a sample representation of the GUI when the surgeon selects a 3D model of another patient, as described above, from the historical data of patients for viewing side-by-side with an image of the subject patient The GUI may include different icons or radio buttons, each programmed to activate execution of respective functionalities. Or example, "Review Example" is an icon used by the surgeon to scroll through data of previous patients, enabling the surgeon to apply filters on the data of at least one of the previous patients data or images. The filters may comprise, but not be limited to, "show surgical procedures with highest success rates' and 'show previous patients having patient histories similar to the subject patient."

As another example, the "select path" icon allows the surgeon to use a tracking device, such as a mouse and a pointer, to select surgical paths. The surgical paths may include lines or tracks displayed as graphical overlays on a 3D model selected by the surgeon. The surgeon may select a surgical path and then view all metadata associated with the 3D model displayed beneath the surgical path. The surgeon may also be able to rotate the 3D model around the surgical path, and may thus view the 3D model from numerous perspectives.

As another example, the "Highlight Path" icon may be used to enhance each image present in the stored data pertaining to previous patients and the subject patient, to show the surgical paths. The surgeon may use the tracking device to select and highlight one surgical path from the stored surgical paths, using the "Highlight path" icon. The "Highlight path" icon may also allow the surgeon to turn on, turn off, and highlight elements present in the 3D model, such as arteries, muscle groups, bone, and skin.

As another example, the "Review Patient" icon may be used by the surgeon to view and to scroll through details of the subject patient, including numerous 3D models present in the 3D model database 110. The "Review Outcomes" icon allows the surgeon to view outcomes associated with the 3D models of the previous patients, as seen in section A under "Patient Outcome." The "Review Outcomes" option may be available while the surgeon is viewing diagnostic data of the previous patients having a medical history similar to the subject patient.

As another example, the "Copy Path" icon may be used by the surgeon to select and copy the surgical path, using the tracking device. For example, when the surgical path is copied, an image of a copied surgical path is shown on a left side of section B; also, when the copied surgical path is to be pasted, the image of the subject patient is shown to either the left or the right side of section B. The surgeon may also be able to modify the copied surgical path using a resizing or editing function.

As another example, the "Highlight Boundaries" icon may be used by the surgeon to select the surgical path and successively highlight a boundary of the surgical path, using the tracking device. The boundary may be virtually created by drawing on the image. After the creating, the boundary may be labeled. For example, a first bone in the surgical path may be labeled as "first bone" and an area of the surgical path for which a warning was issued may be labeled as "caution area."

In at least one example, the surgeon may click on a displayed element or feature, such as an artery, and the entire artery may light up by using color filtering or image recognition techniques. Accordingly, the surgeon may easily select and label the boundary as, as a non-limiting example, "muscle to be moved." In another example, the boundary may be highlighted by use of a voice command that is processed using an AI search. The substance of the voice command may be searched in all of the images present in the real-time health record unit 108 or the 3D model database 110. For example, the voice command may include "highlight boundaries labeled caution areas by expert surgeons," and thus all such boundaries may be retrieved and highlighted for the surgeon to view.

As yet another example, the "Define Boundaries" icon ay be used by the surgeon to select the surgical path, highlight the boundary, and define the boundary. For example, the boundary may be labeled as "first bone" and may be defined as "2 mm." Such definition of the boundary may reference the first bone in the surgical path and a virtual boundary of 2 mm may need to be drawn around the highlighted boundary.

As another example, the "Determine Boundaries" icon may be used by the surgeon to select the surgical path, highlight the boundary, define the boundary, and further define the boundary. For example, the boundary labeled as "first bone" and defined as "2 mm" may be further defined as being critical or non-critical, indicating whether it is advisable to move across the boundary or not. Such information may be used to determine criticality of haptic interfaces and haptic types.

As another example, the "Determine Haptic Types and Amounts" icon may be used by the surgeon to select types of haptics to be employed, and to set an intensity of haptic feedback. In at least one example, the haptics may be selected from a buzzer, vibration, sound, visual, and AI. Further, the intensity of haptic feedback may indicate an amount of time, speed of vibration, and volume of the buzzer. The "Determine Haptic Types and Amounts" icon may allow the surgeon to select, from among a set of choices, types of haptic interfaces (such as buzzer and vibration), positioning of the haptic interfaces (such as on the drill, on the scalpel, or the surgical robot), and the intensity of haptic feedback.

As another example, the "Copy Boundaries" icon may be used by the surgeon to select and copy the boundary, using the tracking device. In at least one example, while the Copy Boundary command is initiated, an image of a copied boundary is shown on a left side of section B. Further, the image of the subject patient, where the copied boundary is to be pasted, is shown on a right side of section B. The surgeon may also be able to modify the copied boundary using a resizing or editing function.

The flowcharts of above explained FIGS. FIGS. 3A, 3B, and 4 show the architecture, functionality, and operation for providing assistance to a surgeon for minimizing errors during a surgical procedure. In this regard, each block may represent a module, segment, or portion of code, which comprises one or more executable instructions for implementing the specified logical function(s). It should also be noted that in some alternative implementations, the functions noted in the blocks may occur out of the order noted in the drawings. For example, two blocks shown in succession in FIG. 4 may in fact be executed substantially concurrently or the blocks may sometimes be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine.

Figure 6A:
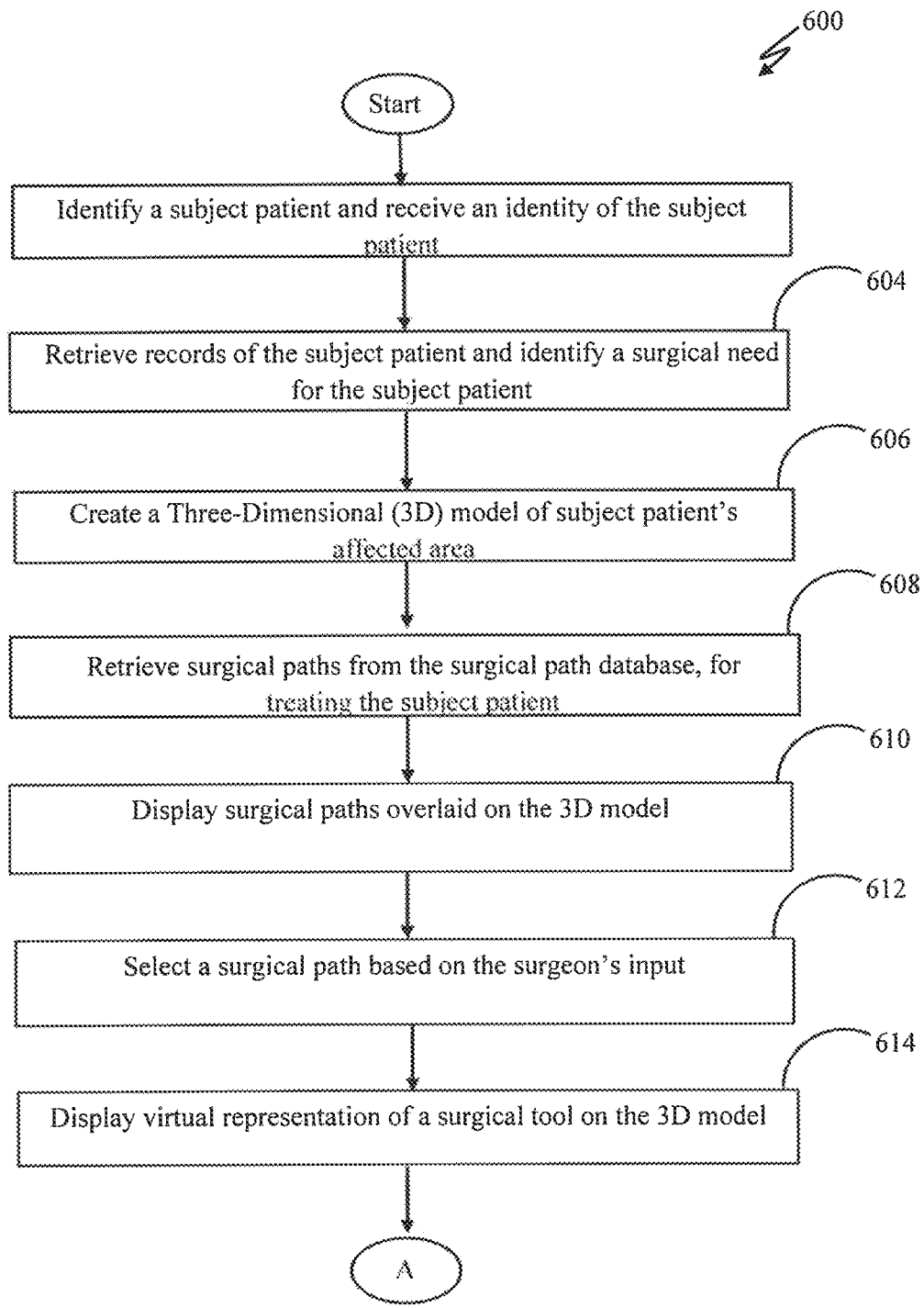
FIGS. 6A and 6B collectively illustrate a flowchart 600 showing a method performed by a Virtual Reality (VR) simulation module 2208 of system 102, according to an embodiment.
Figure 6B:
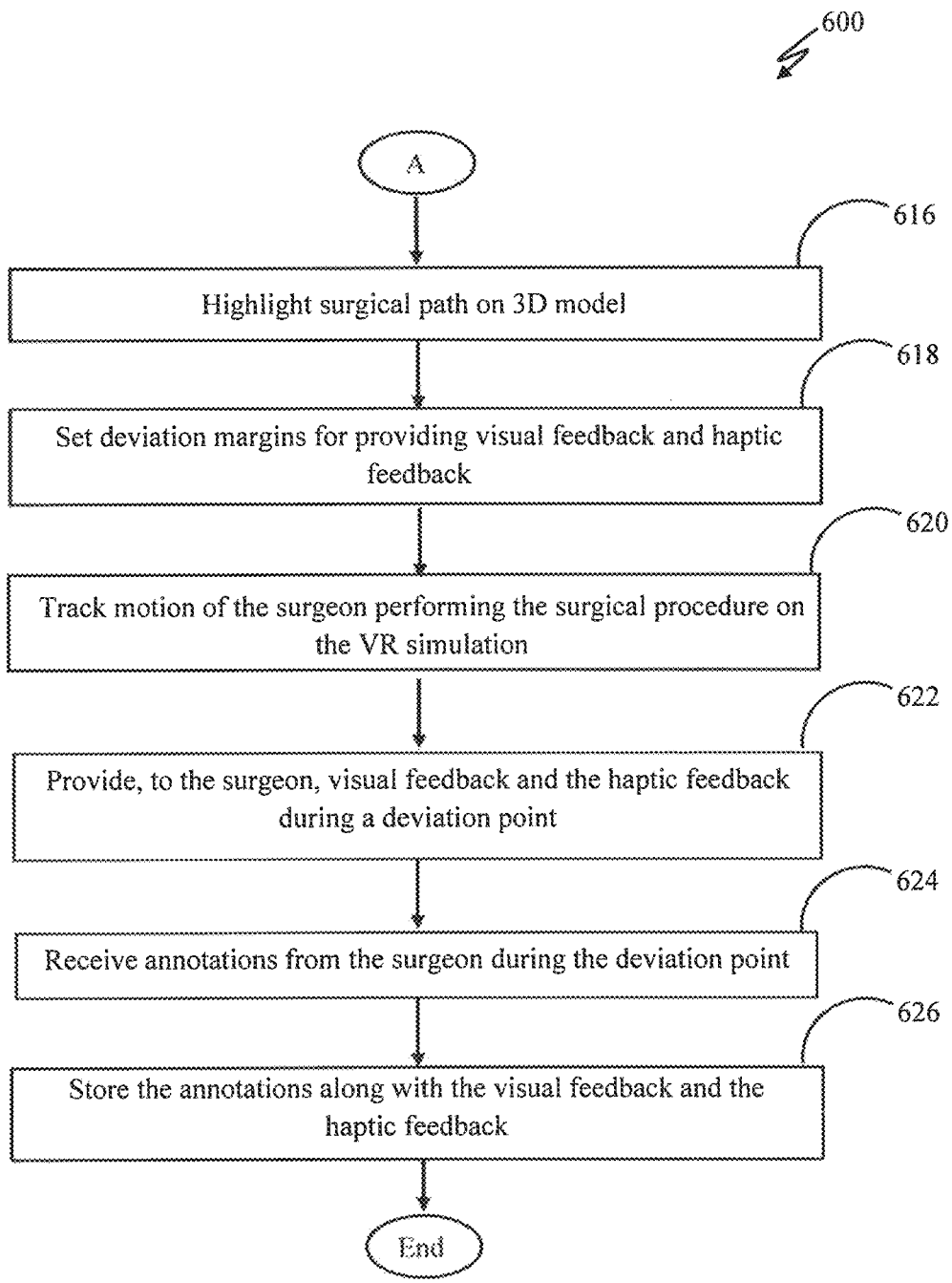

Flowchart 600 in FIGS. 6A and 6B is described hereafter to explain at least one embodiment of the functionality of VR simulation module 2208, also shown and described with regard to FIG. 2B.

A surgeon may need to log-in to the VR simulation module 2208. The surgeon may log-in using his credentials, i.e. a user name and a password, a user identity, biometric credentials, etc. At step 602, the VR simulation module 2208 may allow the surgeon to identify a subject patient and receive an identity of the subject patient. The VR simulation module 2208 may facilitate retrieval of records for the subject patient from Electronic Health Records (EHR) stored in the real-time health record unit 108, as shown and described with regard to FIGS. 1A and 1B. The records may include at least one of an image data and/or a diagnostic data.

At step 604, records of the subject patient may be retrieved and a recommended surgery may be identified. The surgery recommended for the subject patient may be identified based at least on an analysis of a diagnosis for the subject patient. At step 606, the VR simulation module 2208 may facilitate creation of a 3D model of an affected area/body part of the subject patient. The 3D model may be created based at least on the records which are retrieved from the Electronic Health Records (EHR), e.g., using at least one image captured during the diagnosis of the subject patient.

At step 608, surgical paths may be retrieved from the surgical path database 1110, shown and described with regard to FIG. 1B. The surgical paths may be used for performing the surgical procedure on the subject patient. For example, the subject patient may need a knee replacement. The surgical procedure for repairing the knee may include a cadaver graft, patellar tendon graft, and different surgical paths for performing the surgical procedures. All possible surgical paths for repairing of the knee may thus be retrieved from the surgical path database 1110, at step 608.

At step 610, the VR simulation module 2208 may facilitate the display all the surgical paths overlaid on the 3D model. The surgeon may select a surgical path from the displayed surgical paths. At step 612, as an example, the surgical path may be selected based on the surgeon's input.

At step 614, the VR simulation module 2208 may facilitate the display of the virtual representation of a surgical tool on the 3D model. For example, the surgical tool may be a robotic surgical arm with a drill attachment, scalpel, or any other surgical tool required by the surgeon. At step 616, the VR simulation module 2208 may cause the surgical path on the 3D model to be highlighted, e.g., the surgical path may be displayed in green color on the 3D model.

In at least one example embodiment, the user may start performing a VR simulation of the surgery using the VR surgical practice system 1120, also shown and described with regard to FIG. 1B. The VR surgical practice system 1120 may allow simulation of surgical procedures, and may present one or more virtual organs on which the surgeon is to operate. A vital organ may comprise multiple elements and each element may have neighbouring elements. A plurality of tensioned connections may connect the neighbouring elements with the vital organ, such that force applied on one element propagates via respective neighbouring elements and thus providing a distributed reaction over the vital organ.

The VR surgical practice system 1120 may also comprise a physical manipulation device to be manipulated by the user, and a tracking arrangement to track the physical manipulation device and translate motion of the physical manipulation device into application of forces onto the virtual organ. The VR surgical practice system 1120 may enable the simulation of moving, cutting, suturing, coagulations, and other aspects of surgical procedure for different organs. Thus, the VR surgical practice system 1120 may facilitate a realistic practice of the surgical procedure.

While performing the surgery, at step 618, the VR simulation module 2208 may allow the surgeon to set deviation margins for providing a visual feedback and a haptic feedback during the surgical procedure. In at least one example, the surgeon may define an intensity of vibration to be provided on the haptic feedback hand controller or an actual surgical drill e.g., the surgeon may define the intensity of vibration from 1 to 10, from least intensity to highest intensity. In at least one embodiment, the intensity may increase or decrease based on a variation of the haptic feedback hand controller or an actual surgical drill from the surgical path. In another example embodiment, the vibration settings may be accompanied with color change to provide visual feedback, e.g., a red light may be presented upon a deviation of "2 mm" from the surgical path or dark red may be presented upon a deviation of "2 mm" from the surgical path in a critical area.

At step 620, the VR simulation module s208 may facilitate tracking of the motion of the surgeon. The motion of the surgeon may be tracked while the surgeon performs the surgical procedure over the VR simulation, using the VR surgical practice system 1120. In at least one example embodiment, motion of the surgeon may be tracked using data received from camera integrated AR glasses 1116 worn by the surgeon. Further, motion of the surgical tool relative to the surgical path may also be tracked.

In at least one example implementation, at step 622, if, while the surgeon performs the surgical procedure using the VR surgical practice system 1120, the surgical tool may deviate from the surgical path, the visual feedback and the haptic feedback may immediately be provided to the surgeon, upon occurrence of the deviation point. The deviation point may be indicated by a deviation of the surgical tool from the surgical path, within the deviation margins. In one example, the visual feedback may be provided by modifying a color of the highlighted surgical path on the 3D model. For example, as discussed above, the highlighted surgical path may be shown in green. For non-critical areas, the color may change from green to yellow. As another non-limiting example, for a critical area, the color may change from yellow to red, indicative of a warning.

Similarly, the VR simulation module 2208 may cause the haptic feedback to be provided to the surgeon through the haptic feedback hand controllers. For example, a vibration frequency may be set at a lower frequency for non-critical paths, whereas the vibration frequency may be more intense for more critical paths, and the strength maybe higher based on the deviation of the surgical tool from the surgical path.

At step 624, the VR simulation module 2208 may allow the surgeon to set one or more annotations at the deviation point. The annotations may be provided either by accessing the system 102 or the user device 1118. The annotations may include, but are not limited to, text, audio notes, instructions to pull up specific medical data from patient's Electronic Health Records (EHR), and Audio-Video files related to the procedure.

At step 626, the VR simulation module 2208 may facilitate storage of the annotations, along with the visual feedback and the haptic feedback, in the surgical annotation database 1112. Any change in the vibration settings along with the timestamp may be stored in the vibration database 1114. The annotations may need to be presented to the surgeon, upon occurrence of the deviation point, while performing a real surgical procedure. A reference to the deviation point may be made using time-stamps. The annotations may be presented based on the time-stamps associated with the annotations.

Successively, the VR simulation module 2208 may display a list of the deviation points, the annotations, and vibration settings, defined during the virtual reality simulation. Thereafter, the VR simulation module 2208 may facilitate approval of the surgical path, the surgical procedure, and the annotations, by the surgeon.

Figure 7:
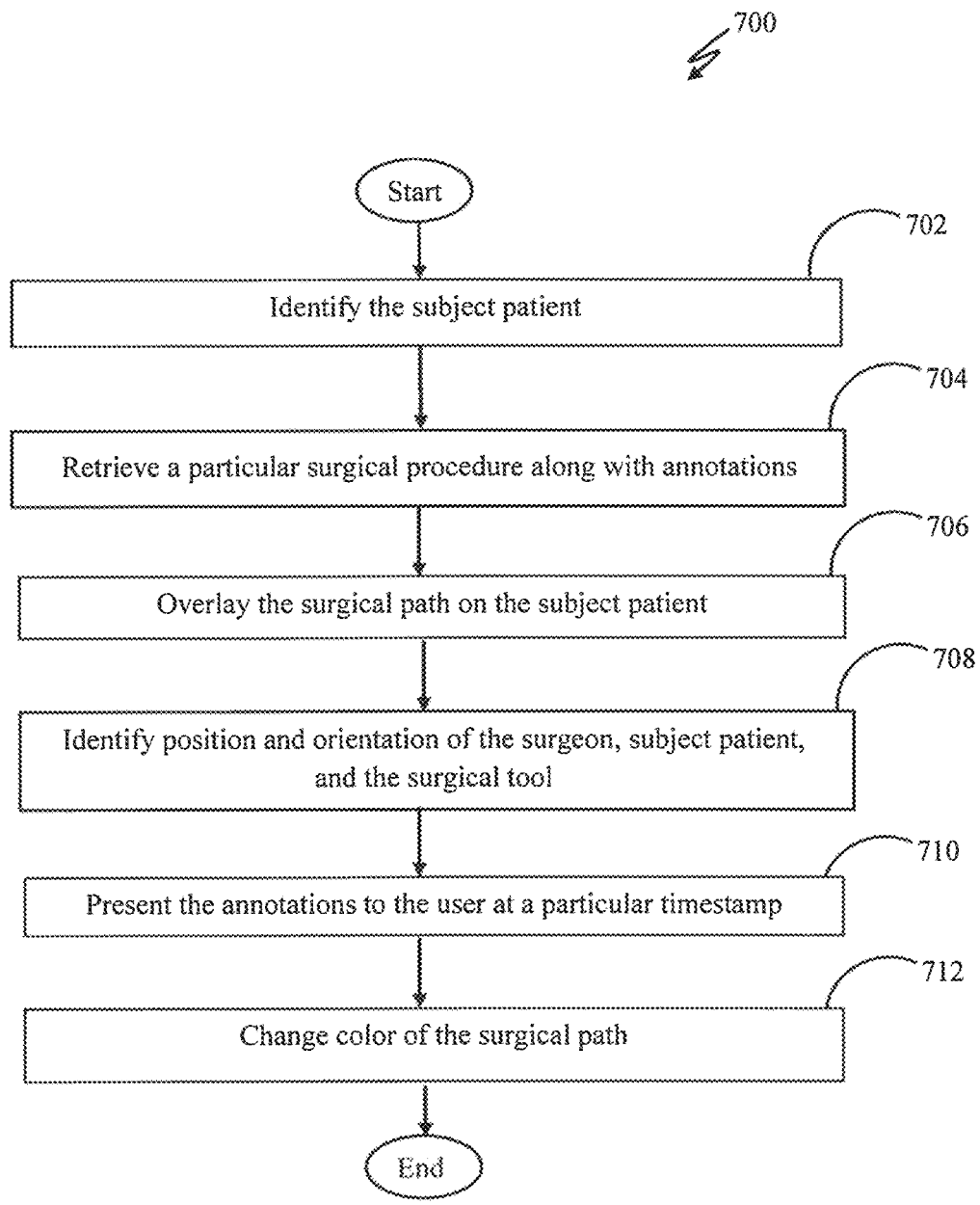
FIG. 7 illustrates a flowchart 700 showing a method performed by an Augmented Reality (AR) surgical assistance module 2210 of system 102, according to an embodiment.

Flowchart 700 of FIG. 7 is described hereafter to explain at least one embodiment of assistance module 2210 of the system 102, also shown and described with regard to FIGS. 2A and 2B. The AR surgical assistance module 2210 may provide support to the surgeon during a real surgical procedure on the subject patient.

A surgeon may log-in to the AR surgical assistance module 2210 using his credentials, e.g., a user identity, a password, biometric credentials, etc. At step 702, the AR surgical assistance module 2210 may facilitate subject patient identification for the surgeon or other user. At step 704, the AR surgical assistance module 2210 may store and facilitate retrieval of details of a particular surgical procedure, e.g., the surgical path along with the annotations, from the surgical annotation database 112.

At step 706, the surgical path chosen by the surgeon may be overlaid on the subject patient. At step 708, a position and an orientation of the surgeon, subject patient, and the surgical tool may be identified, using the camera integrated AR glasses 1116. In at least one alternate embodiment, operating room cameras may be utilized to identify the position and the orientation of the surgeon, subject patient, and the surgical tool.

In at least one example embodiment, at step 710, the surgeon may begin the surgery, and while performing the surgery, the annotations may be presented to the user. In at least one example, an appropriate time to present the annotations may be determined based on time stamps set by the surgeon during the training phase. For example, an annotation may be set to be presented five minutes into the surgical procedure. In another case, an appropriate time to present the annotations may be determined based upon initiation of a step of the surgical procedure. For example, an annotation may be set to be presented during initiation of a third step of the surgical procedure. Each step of the surgical procedure may be monitored by the camera integrated AR glasses 1116. Thus, the system 102 may accordingly present the annotation to the surgeon at a predetermined surgical step.

The annotations may help the surgeon in storing important details related to any step of the surgical procedure. Such details may be presented to the surgeon, at designated moments, as reminders and/or warnings. Thus, the surgeons may be assisted by their own input recorded during a training session prior to the actual surgical procedure. Thus the surgeon's accuracy and efficiency are enhanced by allowing them to heed every minute yet essential detail, thus reducing occurrence of errors.

In at least one example embodiment, at step 712, while the surgical tool deviates from the surgical path, the color of the highlighted surgical path may change. For example, in a low priority zone, the color of the surgical path may change from green to yellow while the surgical tool begins to deviate from the surgical path. Further, the vibration settings may be changed from low to medium strength, gradually over time. In another example, in a high priority zone, the color of the surgical path may change from yellow to red, and the haptic feedback is provided to the surgeon during deviation of the surgical tool from the path.

Figure 8:
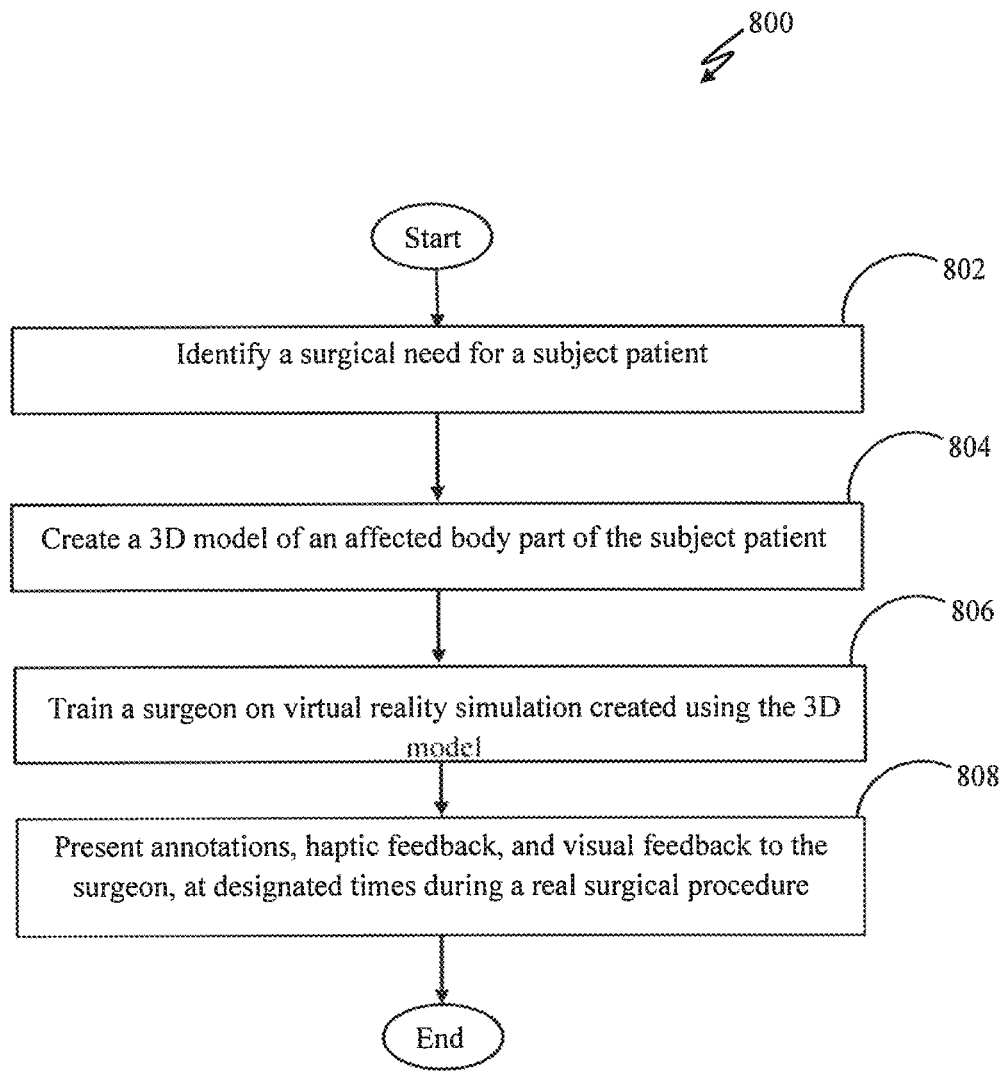
FIG. 8 illustrates a flowchart 800 showing a method for assisting the surgeon with the visual feedback and the haptic feedback during the surgical procedure, according to an embodiment.

Flowchart 800 in FIG. 8 is described hereafter to explain at least one example of providing assistance to a surgeon using visual feedback and haptic feedback during a surgical procedure.

In flowchart 800, each block may represent a module, segment, or portion of code, which comprises one or more executable instructions for implementing the specified logical function(s). It should also be noted that in some alternative implementations, the functions noted in the blocks may occur out of the order noted in the drawings. For example, two blocks shown in succession may in fact be executed substantially concurrently or the blocks may sometimes be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine.

At step 802, a recommended surgery for a subject patient may be identified, based on the medical condition of the patient.

At step 804, a 3D model of an affected body part of the subject patient may be created using at least one image captured during diagnosis of the subject patient. The images may be gathered from different sources such as a digital camera, X-ray device, and Magnetic Resonance Imaging (MRI) device.

At step 806, a VR simulation may be created for training a surgeon using the 3D model. During the training, a virtual representation of the surgical tool on the 3D model may be displayed, and the surgical path shown on the 3D model may be highlighted. Further, deviation margins may be set based on surgeon's input, for providing a visual feedback and a haptic feedback to the surgeon, during a real surgical procedure. Further, the VR simulation module 2208 may facilitate tracking of motion of the surgeon while the surgeon operates, over the virtual reality simulation. Based on the deviation of the surgical tool from the surgical path, the VR simulation module 2208 may facilitate the provision of at least one of the visual feedback and the haptic feedback to the surgeon, at a deviation point. Further, the surgeon may set one or more annotations at the deviation points. Thereafter, the one or more annotations may be stored along with the visual feedback and the haptic feedback in the surgical annotation database 1112.

At step 808, the annotations may be presented to the surgeon along with the visual feedback and the haptic feedback at designated moments. The annotations may provide assistance to the surgeon by providing reminders and/or warnings at designated moments during surgery.

Figure 9:
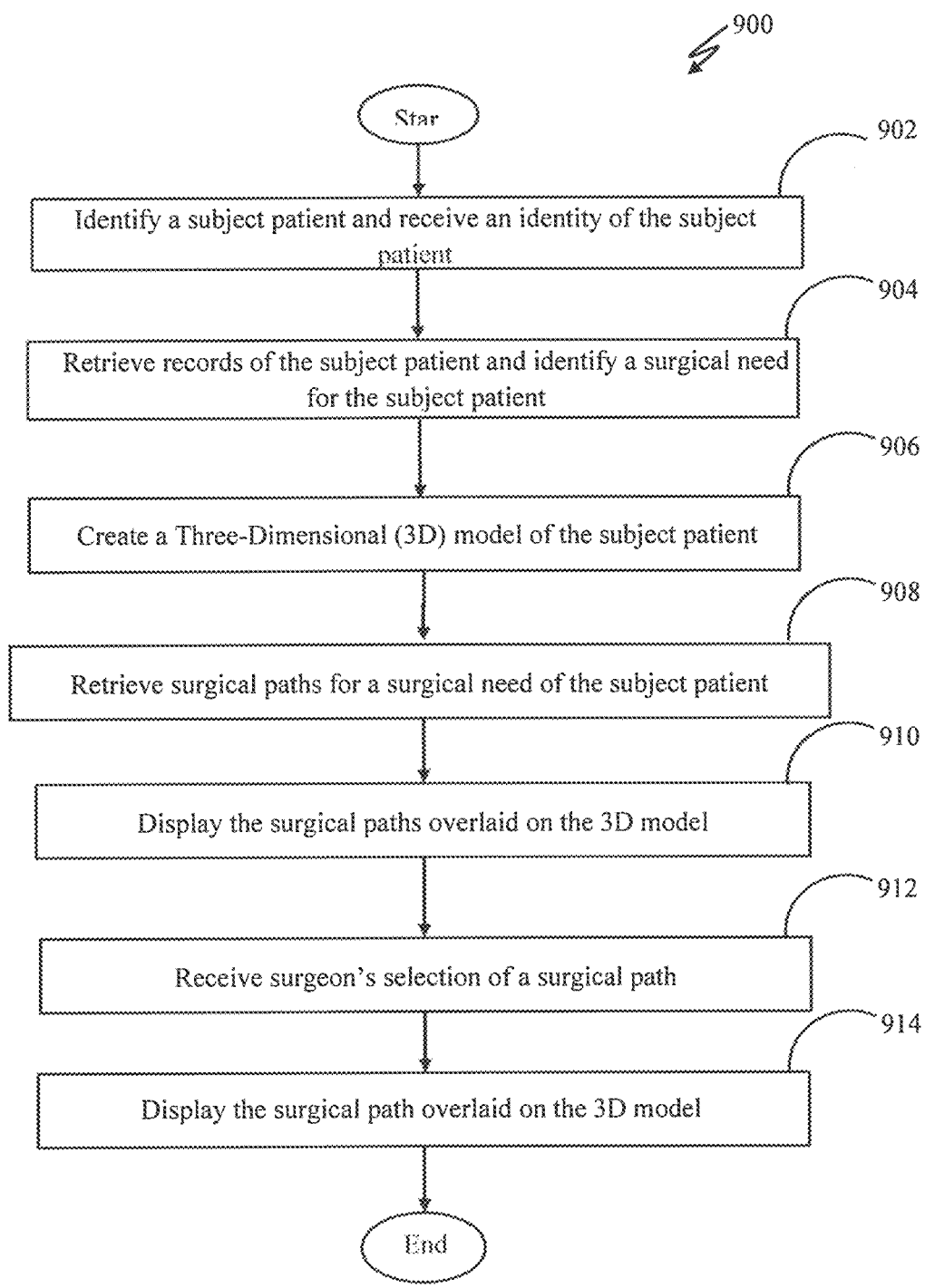
FIG. 9. illustrates a flowchart 900 showing a method executed by a surgical planning module 2082 of system 102, according to an embodiment.

Flowchart 900 in FIG. 9 is described hereafter to explain at least one embodiment of the surgical planning module 2082, as shown and described with regard to FIG. 2C.

A surgeon may asked to log-in to the system 102 using authentication details, such as a user identity, a password, biometric credentials, etc. The surgeon may log-in to the system 102 either by accessing the interface 204 of the system 102, as shown and described with regard to FIGS. 2A, 2B, and 2C, or by accessing a user device 1181 connected to the system 102. Other non-limiting examples of the user device 118 may be any other device such as a laptop, a desktop, a tablet, a phablet, or other such devices known in the art.

At step 902, the surgical planning module 2082 may facilitate subject patient identification for the surgeon. The surgical planning module 2082 may store and facilitate retrieval of identification details of the subject patient from the real-time health record unit 108, shown and described above with regard to FIGS. 1A, 1B, and 1C.

At step 904, records of the subject patient may be retrieved and a surgical procedure may be recommended for the subject patient, based on analysis of the records of the subject patient. At step 906, a 3D model of the subject patient may be prepared, from the images captured using different sources, as described above. Further, the 3D model may be created using known image recombination techniques.

In at least one example embodiment, at step 908, surgical paths may be retrieved for the surgical need of the subject patient, from the surgical path database 1121. Each surgical path may represent a line drawn from one point to another point, in an image of a body part, having been previously defined by the surgeon, other expert, or stored in the surgical path database 1121. The surgical path database 112 may facilitate analysis and store images of a particular operative region of multiple patients having previously undergone particular surgeries and outcomes thereof. The surgical path database 112 may facilitate retrieval, for or by the surgeon, all previously used surgical paths, unique surgical paths, and frequently used surgical paths along with their respective outcomes.

At step 910, the surgical paths may be displayed by overlaying on the 3D model, using the Augmented Reality (AR) display 1161, shown and described with regard to FIG. 1C. At step 912, system 102 may facilitate selection of a surgical path from the surgical paths, based on a first input provided by the surgeon. At step 314, the surgical path, selected by the surgeon, may be displayed as overlaid on the 3D model.

In at least one example embodiment, the subject patient may need to get a ruptured Achilles tendon repaired, and images of the subject patient's ankle may be used to create a 3D model. Successively, all surgical paths for performing a surgical procedure on the subject patient's ankle may be retrieved from the surgical path database 1121. All the surgical paths may be displayed over the 3D model of the subject patient's ankle.

In at least one example implementation, the surgeon may select a surgical path from among the surgical paths overlaid on the 3D model of the subject patient's ankle. The surgeon may select the surgical path based upon medical results of other patients, previously operated using the surgical path. Post selection, the surgical path may be received and displayed as overlaid on the 3D model of the subject patient's ankle.

In at least one example implementation, the surgical path selected by the surgeon may be stored in the procedure database 1101, as facilitated by the surgical planning module 2082. Further, the system 102 may receive and store annotations or comments provided by the surgeon. The annotations may be present in either of a text, audio, and image form, for being presented to the surgeon during the surgical procedure, through the AR display 1161.

Figure 10:
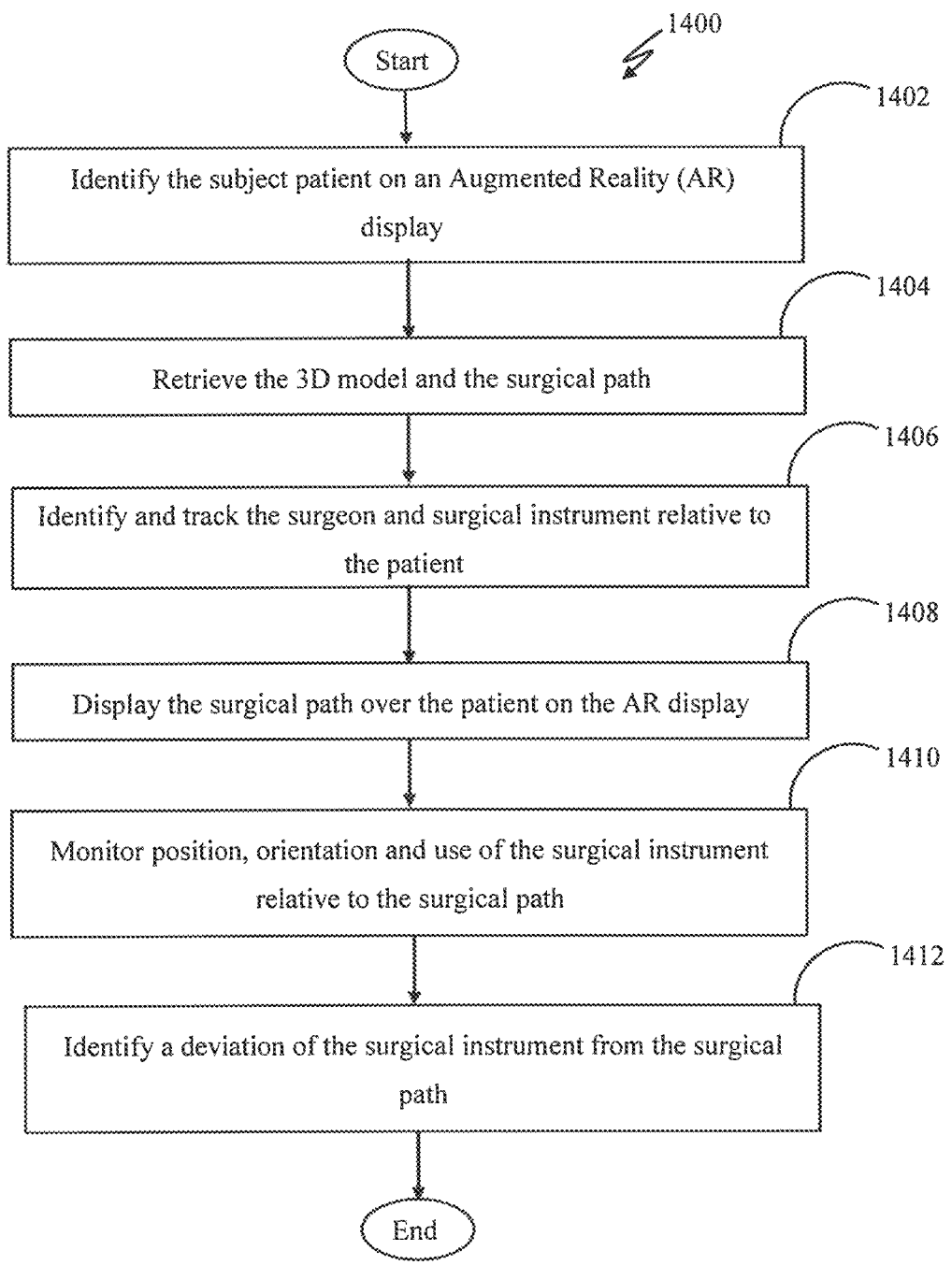
FIG. 10 illustrates a flowchart 1400 showing a method executed by a surgical analysis module 2102 of system 102, according to an embodiment.
Figure 11:
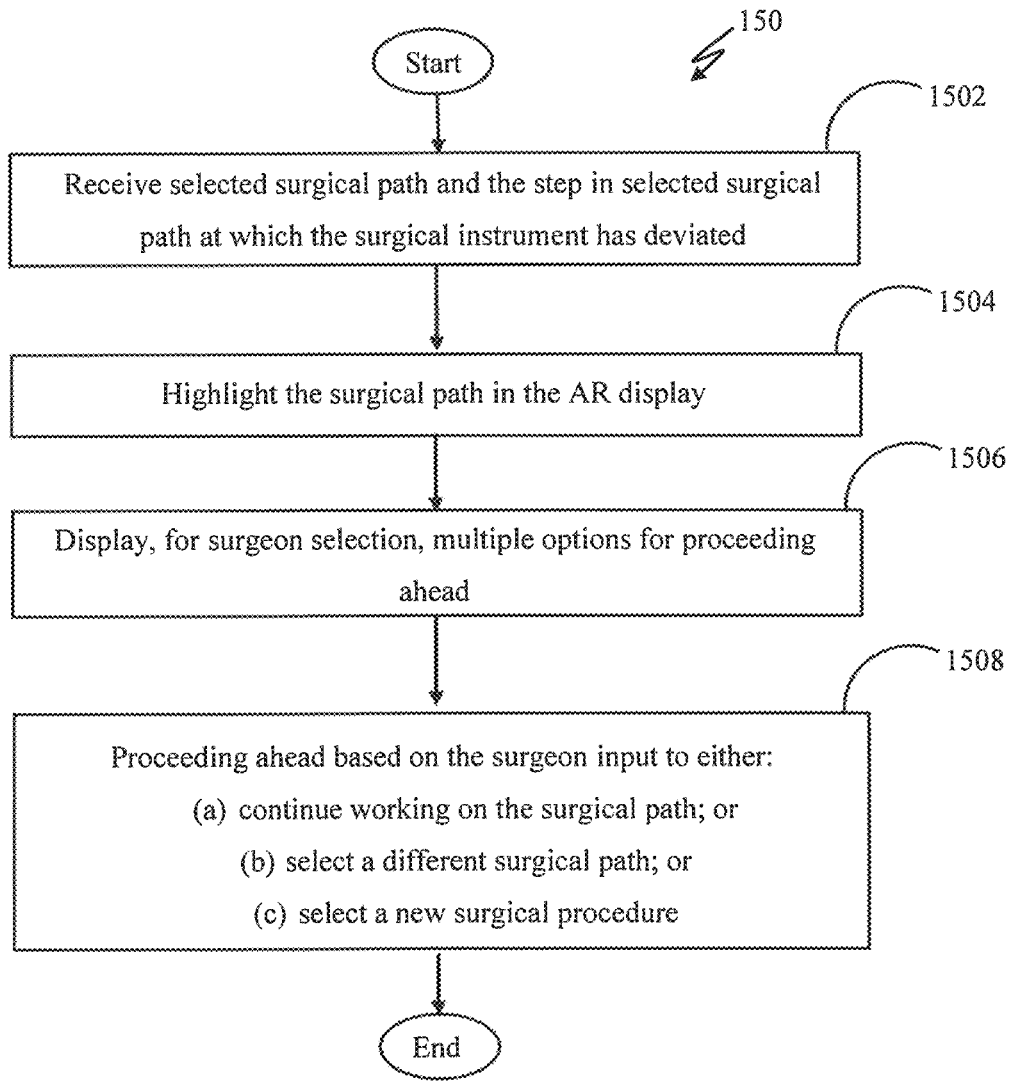
FIG. 11 illustrates a flowchart 1500 showing a method executed by a surgical adjustment module 2122, according to an embodiment FIGS. 12A and 12B collectively illustrate a flowchart 1600 showing a method executed by system 102, for guiding the surgeon during the surgical procedure, according to an embodiment.

Flowchart 1400 in FIG. 10 is described hereafter to explain at least one embodiment of surgical analysis module 2102, also shown and described with regard to FIG. 2C.

Before performing surgery, the surgeon may log-in to the system 102 using authentication details, such as a user identity, password, biometric credentials, etc., by accessing the interface 204 of the system 102, both shown and described with regard to FIGS. 2A, 2B, and 2C, or by accessing the user device 1181 connected to the system 102.

At step 1402, the surgeon may identify the subject patient on the AR display 1161. At step 1402, the 3D model and the surgical path may be retrieved. At step 1406, data from the operation room camera(s) 114 and the sensor(s) 120 may be used to identify and track the surgeon and any surgical instrument provided for the surgical procedure. At least a portion of data captured by the sensor(s) may be selected for display on the AR display 1161.

At step 1408, the surgical path overlaid on the 3D model may be displayed on the AR display 1161. In at least one example, at step 1410, the operating room camera(s) 1141 may also be used to track the position, and orientation of the surgeon and the surgical instrument, relative to the subject patient. At step 1412, the surgical analysis module 210 may identify an anomaly or a deviation of the surgical instrument from the surgical path.

In at least one example embodiment, an alert may be raised while the surgical instrument deviates from the surgical path based on pre-defined conditions stored in the memory 206. The pre-defined conditions may include, for example, a surgeon or surgery attendee holding a surgical instrument beyond a fixed step, usage of a wrong surgical instrument by a surgeon or surgery attendee, a missing surgical instrument, picking a surgical instrument not included in the plan for use at a particular step, picking up of a defective or contaminated surgical instrument, using a surgical instrument in a wrong place during the procedure, using a surgical instrument at an inappropriate time, deviation in alignment of the surgical instrument relative to a surgical path or other conditions that may cause or create an adverse event.

Flowchart 500 in FIG. 5 is described hereafter to explain at least one embodiment of surgical adjustment module 2122, also shown and described with regard to FIG. 2C.

Once an alert has been generated by the surgical analysis module 2102, at step 1502, the surgical adjustment module 212 may receive data from the surgical analysis module 2102, including, but not limited to, a patient identification (ID), the surgical path, and a step in the surgical path, during which the surgical instrument deviated. At step 1504, the surgical path may be highlighted in the AR display 1161. For example, the colour of the surgical path may be changed from green to red, to highlight the deviation.

At step 1506, multiple options for proceeding ahead may be presented before the surgeon. In at least one example embodiment, the multiple options presented before the surgeon may include a) continue working on the same surgical path, b) select a different surgical path, and c) select a new surgical procedure. At step 1508, the surgical adjustment module 2122 may accept a second input provided by the surgeon, to proceed.

In at least one example embodiment, the deviation from the surgical path may be due to an error, a physical abnormality, an emergency, or some unexpected development during the surgical procedure. For example, the surgeon may be operating on the ruptured Achilles tendon and the deviation may arise due to presence of an infected tissue. Post occurrence of the deviation, the surgical adjustment module 2122 may cause a prompt to be provided to the surgeon to choose between working on the surgical path, selecting a different surgical path, or selecting a new surgical procedure. In one example implementation, the surgeon may choose to continue with a new surgical procedure, for example, a debridement procedure. The surgical planning module 2082 may facilitate retrieval of surgical paths for debridement procedures of an ankle from the surgical path database 1121. The surgical paths may be displayed, overlaid on the 3D model of the subject patient, on the AR display 1161. In at least one example implementation, the surgeon may select the new surgical path by interacting with the user device 1181.

In another exemplary embodiment, the surgeon may choose to proceed using a different surgical path. The surgical path database 112 may facilitate retrieval of surgical paths for the surgical procedure and filtering out of surgical paths that do not overlap a waypoint in the surgical path. The waypoint may be a point in the surgical path, where the deviation of the surgical instrument occurred. Post filtering, the surgical paths may be displayed on the AR display 1161, overlaid on the 3D model of the subject patient.

In another exemplary embodiment, the surgeon may choose to continue working along the surgical path. The surgical adjustment module 2122 may facilitate highlighting of the waypoint in the surgical path on the AR display 1161. The surgeon may adjust the surgical instrument relative to the waypoint in the surgical path and may continue working along the surgical path.

Figure 12A:
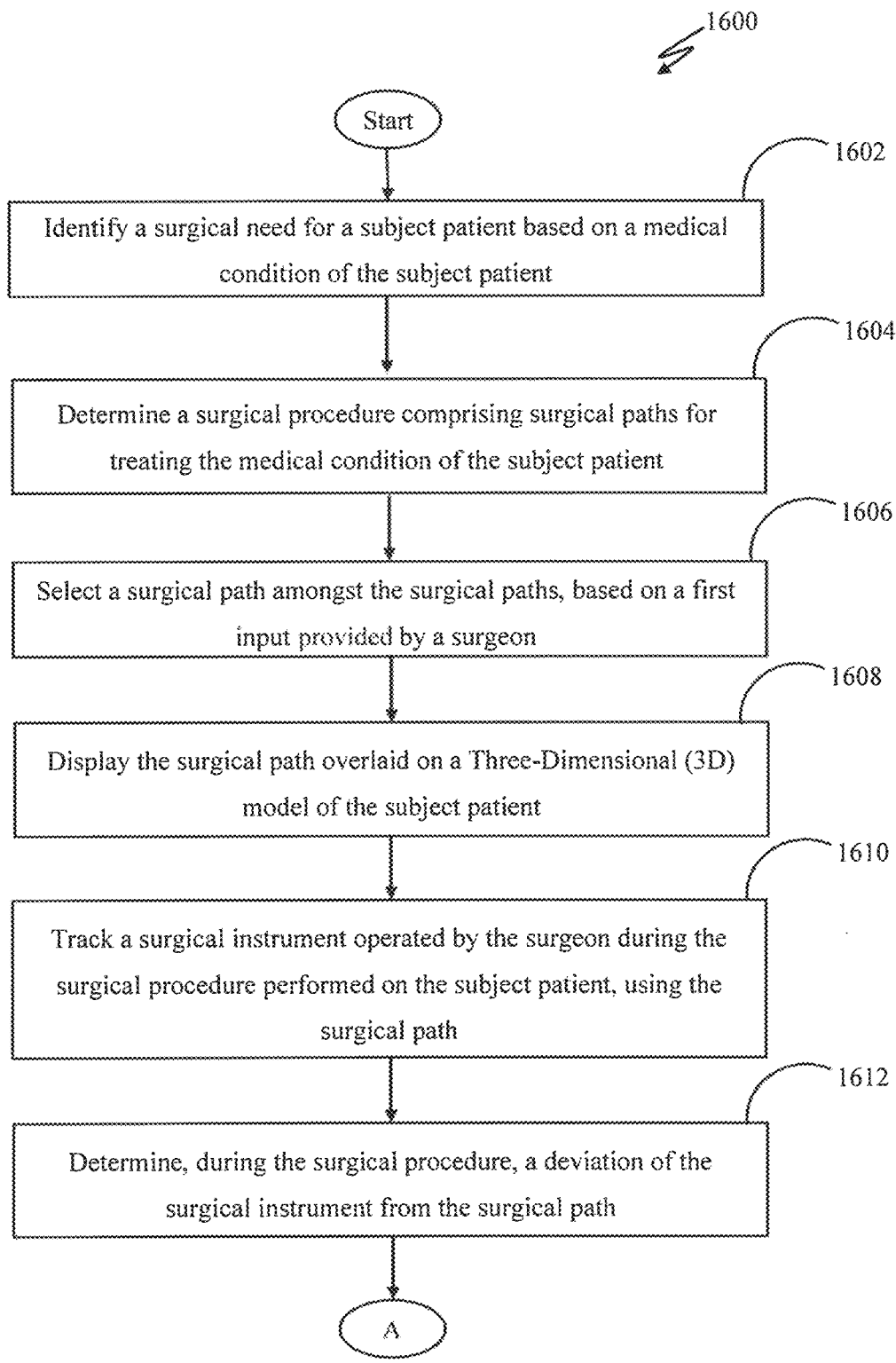
Figure 12B:
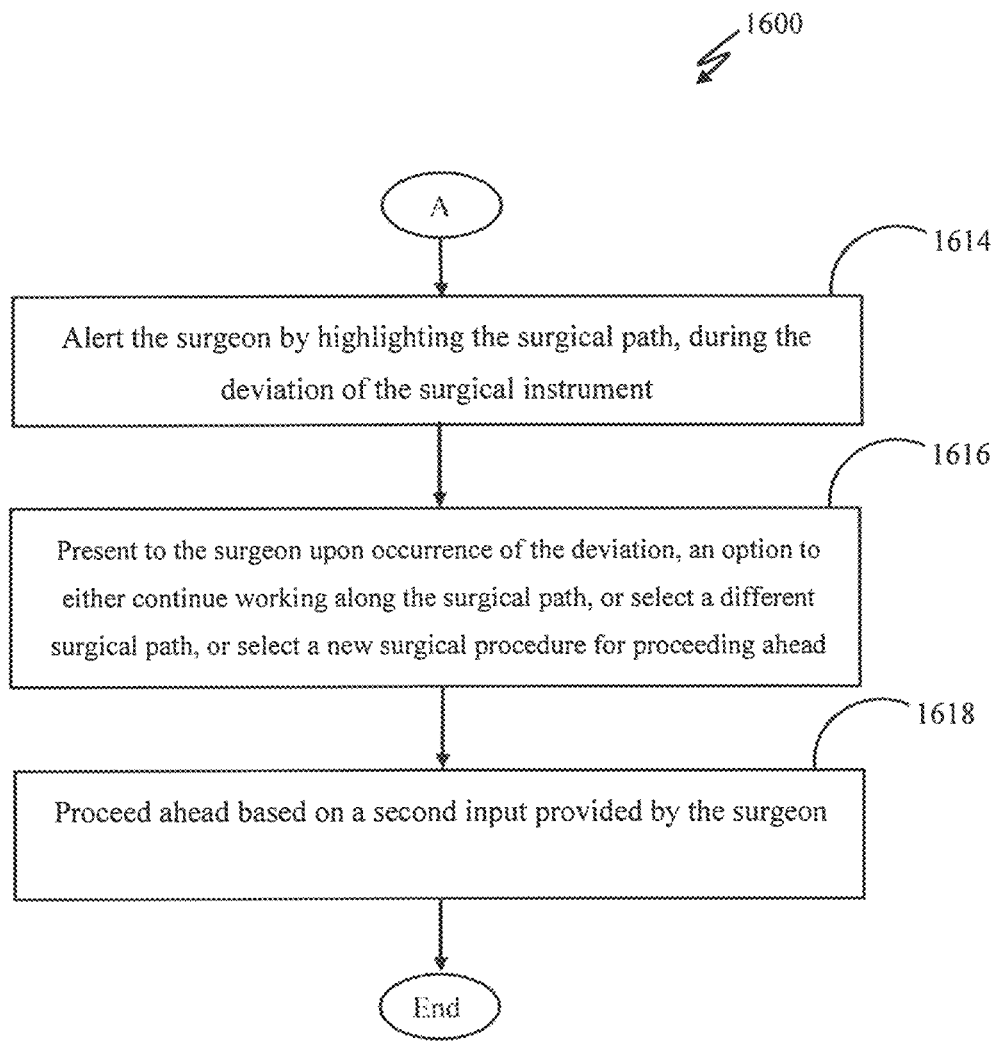

Flowchart 1600 in FIGS. 12A and 12B is described hereafter to explain at least one embodiment of a method of guiding a surgeon in a real-time during a medical procedure The flowchart 1600 shows the architecture, functionality, and operation for guiding a surgeon in a real-time during a medical procedure. In this regard, each block may represent a module, segment, or portion of code, which includes one or more executable instructions for implementing the specified logical function(s). It should also be noted that in some alternative implementations, the functions noted in the blocks may occur out of the order noted in the drawings. For example, two blocks shown in succession in FIGS. 12A and 12B may in fact be executed substantially concurrently or the blocks may sometimes be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine.

At step 1602, surgery may be recommended based on a medical condition of the patient.

At step 1604, a surgical procedure, comprising surgical paths, may be determined for the patient.

At step 1606, a surgical path amongst the surgical paths may be identified based on, e.g., a first input provided by the surgeon.

At step 1608, the selected surgical path may be overlaid on a 3D model of the patient and displayed, using a surgical planning module 2082. The 3D model data may be generated using images gathered from different sources such as a digital camera, X-ray device, and Magnetic Resonance Imaging (MRI) device.

At step 1610, a surgical instrument operated by the surgeon may be tracked during the surgical procedure, using, e.g., operation room camera(s) 1141 and sensor(s) 1201.

At step 1612, a deviation of the surgical instrument from the surgical path may be detected during the surgical procedure, using a surgical analysis module 2102.

At step 1614, upon determining the deviation from the surgical path, an alert may be generated to notify the surgeon, using a surgical adjustment module 2122. The alert may be in the form of highlighting the surgical path or changing the colour of the surgical path. For example, the colour may change from green to red.

At step 1616, a second input may be accepted from the surgeon, to either continue working along the same path, to select a different surgical path, or to select a new surgical procedure, using the surgical adjustment module 2122.

At step 1618, the user may be allowed to proceed ahead based on the second input. For example, the surgeon may proceed ahead by selecting a different surgical path, after the deviation occurred on the surgical path. e.g., previous surgical path.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

We claim:

1. A method for providing surgical assistance, the method comprising:
    planning for a surgical procedure for a subject patient having an identified condition by:
    receiving input identifying at least one of a haptic barrier and a hard barrier, wherein the haptic barrier and the hard barrier define a barrier between different types of tissues, wherein the haptic barrier defines a barrier for a first type of tissue selected from the group consisting of musculoskeletal systems and skin systems and the hard barrier defines a barrier for a second type of tissue selected from the group consisting of nervous systems and cardiovascular systems, and
    associating at least one form of feedback with, respectively, the haptic barrier and the hard barrier;
    providing real-time assistance during an actual surgical procedure on the subject patient by:
    monitoring a position of a robotic surgical tool,
    detecting movement of the robotic surgical tool into at least one of the haptic barrier and the hard barrier, wherein a level of cautiousness associated with the first type of tissue defining the haptic barrier is lower than a level of cautiousness associated with the second type of tissue defining the hard barrier,
    providing a haptic feedback when the robotic surgical tool enters into the haptic barrier, and
    completely stopping further movement of the robotic surgical tool into the hard barrier when the robotic surgical tool enters into the hard barrier, until the robotic surgical tool is removed from the hard barrier.

2. The method of claim 1, wherein the haptic feedback is transmitted to an operator of the robotic surgical tool via hand controllers of the robotic surgical tool.

3. The method of claim 1, wherein the haptic feedback is accompanied by at least one of an audio feedback and a visual feedback.

4. The method of claim 1, further comprising:
    logging on to a robotic surgical system with authentication;
    identifying the subject patient to be operated; and
    activating the robotic surgical system configured to perform the surgical procedure.

5. The method of claim 4, further comprising:
    determining a location and orientation of the robotic surgical system using an ultrasound imaging system.

6. The method of claim 5, further comprising:
    scanning an area determined by a selected surgical path using the ultrasound imaging system; and
    scanning the area along the selected surgical path to identify movement of the robotic surgical tool.

7. The method of claim 6, further comprising:
    detecting a distance between the robotic surgical tool and the haptic barrier, and
    issuing an alert when the distance is reaching a predetermined threshold.

8. The method of claim 6, further comprising:
    detecting whether the robotic surgical tool touches the haptic barrier, and
    issuing an alert when the robotic surgical tool touches the haptic barrier.

9. The method of claim 6, further comprising:
    detecting a distance the robotic surgical tool moving into the haptic barrier, and
    issuing an alert when the distance is greater than a predetermined threshold.

10. A non-transitory computer-readable medium having executable instructions stored thereon that, upon execution, cause one or more processors to:
    plan for a surgical procedure for a subject patient having an identified condition by:
    receiving input identifying at least one of a haptic barrier and a hard barrier for different types of tissues, wherein the haptic barrier and the hard barrier define a barrier between different types of tissues, wherein the haptic barrier defines a barrier for a first type of tissue selected from the group consisting of musculoskeletal systems and skin systems and the hard barrier defines a barrier for a second type of tissue selected from the group consisting of nervous systems and cardiovascular systems, and
    associating at least one form of feedback with, respectively, the haptic barrier and the hard barrier; and
    provide real-time assistance during an actual surgical procedure on the subject patient by:
    monitoring a position of a robotic surgical tool,
    detecting movement of the robotic surgical tool into at least one of the haptic barrier and the hard barrier, wherein a level of cautiousness associated with the first type of tissue defining the haptic barrier is lower than a level of cautiousness associated with the second type of tissue defining the hard barrier,
    providing a haptic feedback when the robotic surgical tool enters into the haptic barrier, and
    completely stopping further movement of the robotic surgical tool into the hard barrier when the robotic surgical tool enters into the hard barrier, until the robotic surgical tool is removed from the hard barrier.

* * * * *